US010989718B2

(12) United States Patent
Jara et al.

(10) Patent No.: US 10,989,718 B2
(45) Date of Patent: Apr. 27, 2021

(54) DETECTION OF MISFOLDED ALPHA SYNUCLEIN PROTEIN

(71) Applicants: Board of Regents of the University of Texas System, Austin, TX (US); Amprion, Inc., Houston, TX (US)

(72) Inventors: Claudio Soto Jara, Friendswood, TX (US); Mohammad Shahnawaz, Houston, TX (US); Russell M. Lebovitz, Oakland, CA (US); Benedikt K. Vollrath, San Diego, CA (US)

(73) Assignees: Amprion, Inc., San Francisco, CA (US); The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 14/852,475

(22) Filed: Sep. 11, 2015

(65) Prior Publication Data

US 2016/0077111 A1 Mar. 17, 2016

Related U.S. Application Data

(60) Provisional application No. 62/049,304, filed on Sep. 11, 2014.

(51) Int. Cl.
*G01N 33/68* (2006.01)

(52) U.S. Cl.
CPC . *G01N 33/6896* (2013.01); *G01N 2333/4703* (2013.01); *G01N 2800/2835* (2013.01); *G01N 2800/52* (2013.01)

(58) Field of Classification Search
CPC ....... G01N 33/6896; G01N 2800/2821; G01N 2333/4709; G01N 2500/00;

(Continued)

(56) References Cited

U.S. PATENT DOCUMENTS 7,351,526 B2 4/2008 Soto
8,632,776 B2 * 1/2014 Nordstrom ............. C07K 16/18
424/139.1

(Continued)

FOREIGN PATENT DOCUMENTS

WO 2002004954 A3 10/2002
WO 2014025905 2/2014
WO 2016040903 A1 3/2016

OTHER PUBLICATIONS

Herva ME et al. Anti-amyloid compounds inhibit alpha-synuclein aggregation induced by protein misfolding cyclic amplification (PMCA). J. Biol. Chem. 289 (17):11897-11905 (Apr. 2014).*

(Continued)

*Primary Examiner* — Kimberly Ballard
(74) *Attorney, Agent, or Firm* — Kem Kendrick, LLC; Benjamen E. Kern

(57) ABSTRACT

Methods and kits are provided for amplifying and detecting αS proteins from samples, for example, from patients having Parkinson's Disease. For example, a method for determining a presence of a soluble, misfolded αS protein may include: contacting the sample with a monomeric, folded αS protein to form an incubation mixture; conducting an incubation cycle two or more times on the incubation mixture effective to form an amplified portion of misfolded αS protein; incubating the incubation mixture effective to cause misfolding and/or aggregation of at least a portion of the monomeric, folded αS protein in the presence of the soluble, misfolded αS protein; physically disrupting the incubation mixture effective to at least partly de-aggregate at least a portion of a misfolded αS aggregate present; and determining the presence of the soluble, misfolded αS protein in the sample by detecting at least a portion of the soluble, misfolded αS protein.

22 Claims, 12 Drawing Sheets

(58) Field of Classification Search
CPC ....... G01N 2800/52; G01N 2800/2835; G01N 2800/28; G01N 2800/50

See application file for complete search history.

(56) References Cited

U.S. PATENT DOCUMENTS

| | | | |
|---|---|---|---|
| 9,910,049 | B2 | 3/2018 | Soto et al. |
| 2005/0064505 | A1 | 3/2005 | Soto-Jara et al. |
| 2005/0176078 | A1* | 8/2005 | Allsop ............. G01N 33/57484 435/7.92 |
| 2006/0263767 | A1 | 11/2006 | Castrillon et al. |
| 2007/0218491 | A1 | 9/2007 | Vasan et al. |
| 2008/0118938 | A1* | 5/2008 | Estrada ............. G01N 33/6896 435/7.92 |
| 2009/0163594 | A1 | 6/2009 | Shapiro et al. |
| 2011/0166035 | A1 | 7/2011 | Kleinschmidt et al. |
| 2013/0289022 | A1 | 10/2013 | Ringe et al. |
| 2015/0309054 | A1 | 10/2015 | Diamond et al. |
| 2016/0077112 | A1 | 3/2016 | Soto et al. |
| 2017/0146556 | A1* | 5/2017 | Luehrs ............... G01N 33/6896 |
| 2018/0335438 | A1 | 11/2018 | Soto-Jara et al. |

OTHER PUBLICATIONS

Roostaee A et al. Aggregation and neurotoxicity of recombinant alpha-synuclein aggregates initiated by dimerization. Molecular Degeneration, 2013, 8:5.*
Salvadores N. et al. Detection of misfolded Abeta oligomers for sensitive biochemical diagnosis of Alzheimer's disease. Cell Reports, Apr. 2014, 7:261-268.*
Narkiewicz J et al. In vitro aggregation assays for the characterization of alpha-synuclein prion-like properties. Prion, Jan./Feb. 2014, 8(1), 19-32. (Year: 2014).*
Van Raaij ME et al. Concentration dependence of alpha-synuclein fibril length assessed by quantitative atomic force microscopy and statistical-mechanical theory. Biophys. J. 2008, 95, 4871-4878. (Year: 2008).*
Roostaee A et al. Aggregation and neurotoxicity of recombinant alpha-synuclein aggregates initiated by dimerization. Mol. Neurodegeneration, 2013, 8:5. (Year: 2013).*
Buell AK et al. Solution conditions determine the relative importance of nucleation and growth processes in alpha-synuclein aggregation. PNAS, May 2014, 111(21), 7671-7676. (Year: 2014).*
Giehm L and Otzen DE. Strategies to increase the reproducibility of protein fibrillization in plate reader assays. Anal. Biochem. 2010, 400, 270-281. (Year: 2010).*
Hoyer W et al. Dependence of alpha-synuclein aggregate morphology on solution conditions. J. Mol. Biol. 2002, 322, 383-393. (Year: 2002).*
Ramis R et al. Unraveling the NaCl concentration effect on the first stages of alpha-synuclein aggregation. Biomacromolecules, 2020, 21, 5200-5212. (Year: 2020).*
Garvey M et al. Phosphate and HEPES buffers potently affect the fibrillation and oliomerization mechanism of Alzheimer's Abeta peptide. Biochem Biophys Res Comm, 2011, 409: 385-388.
Jimenez S et al. Disruption of amyloid plaques integrity affects the soluble oligomers content from Alzheimer diseased brains. PLoS One, 2014, 9(12):e114041.
Padayachee ER et al. The novel effect of CFF and APOE4 on aggregation kinetics of Abeta42 in Alzheimer's disease. Alzheier's & Dementia, Jul. 2014, 10 (Suppl. 4):p. 511, Poster Abstract p. 2-108, Alzheimer's Association International Conference 2014.
Paravastu AK et al. Seeded growth of beta-ayloid bifrils from Alzheimer's brad-derived fibrils produces a distinct fibril structure. Proc. Natl. Acad. Sci. USA, 2009, 106(18):7443-7448.
Schmidt M et al. Comparison of Alzheimer Abeta(1-40) and Abeta(1-42) amyloid fibrils reveals similar protofilament strucures. Proc Natl Acad Sci USA, 2009, 106(47): 19813-19818.
Castilla, et al. "Protein Misfolding Cyclic Amplification for Diagnosis and Prion Propagation Studies" Methods Enzymol, 2006, 412, 3-21.
Ghiso J. et al. Alzheimer's soluble amyloid beta is a normal component of human urine. FEBS Lett. 1997, 408:105-108.
Moreno-Gonzalez I et al. Misfolded protein aggregates: Mechanisms, structures and potential for disease transmission. Seminars Cell Dev. Biol. 2011, 22:482-487.
Windblad B et al. Active immunotherapy options for Alzheimer's disease. Alzheimer's Res. Therap. Jan. 2014, 6:7 (12 pages).
Zhou P et al. Immunoassays with protein misfolding cycle amplification; A platform for ultra sensitive detection of antigen. Analytical Chem. 2012, 84:7343-7349.
International Preliminary Report on Patenability issued in PCT application No. PCT/US2015/049840 dated Mar. 14, 2017.
International Search Report and Written Opinion issued in PCT application No. PCT/US2015/049840 dated Feb. 2, 2016.
Atarashi et al. Simplified ultrasensitive prion detection by recombinant PRP conversion with shaking. Nature Methods Mar. 2005 vol. 5. No. 3 pp. 211-212, Especially p. 211 fig 1.
International Preliminary Report on Patentability issued in PCT application No. PCT/US2015/049842 dated Mar. 14, 2017.
International Search Report and Written Opinion issued in PCT application No. PCT/US2015/049842 dated Feb. 2, 2016.
International Search Report and Written Opinion issued in PCT application No. PCT/US2015/049844 dated Feb. 5, 2016.
International Preliminary Report on Patentability issued in PCT application No. PCT/US2015/049844 dated Mar. 14, 2017.
International Search Report and Written Opinion issued in PCT application no. PCT/US18/32962, dated Sep. 26, 2018.
M.Tolnay et al., "The Neuropathological Spectrum of Neurodegenerative Tauopathies", Taylor & Francis Health Sciences, 55(6), Jun. 2003, pp. 299-305.
J. Stöhr et al., "A 31-residue peptide induces aggregation of tau's microtubule-binding region in cells", Nature chemistry, Apr. 3, 2017, 8 pgs.
G. Fairfoul et al., "Alpha-synuclein RT-QuIC in the CSF of patients with alpha-synucleinopathies", Annals of Clinical and Translational Neurology 2016; 3(10) pp. 812-818.
M. Shahnawaz et al., "Development of a Biochemical Diagnosis of Parkinson Disease by Detection of α-Synuclein Misfolded Aggregates in Cerebrospinal Fluid", JAMANeurology, 2017, 74(2):163-172.
E. Saijo et al., "ultrasensitive and selective detection of 3-repeat tau seeding activity in Pick Disease brain and cerebrospinal fluid", Acta Neuropathol (2017) 113: 781-765.
C.M. Wischick et al., "Selective inhibition of Alzheimer disease-like tau aggregation by phenothiazlines", Proc. Natl., Acad. Sci. USA, vol. 93, Oct. 1996, pp. 11213-11218.
P. D. Dinkel, "Seeded Propagation of Tau Fibrils", University of Denver, Nov. 2013, 149 pgs.
A. L. Woerman, "Propagation of prions causing synucleinopathies in cultured cells", PNAS, Aug. 18, 2015, pp. E4949-E4958.
Office action issued in SOTO, U.S. Pat. No. 7,351,526; dated Apr. 13, 2007.
J. Narkiewics, et al., "In Vitro Aggregation Assays of α-Synuclein Prion-like Properties", Prion 8:1, 19-32; Jan./Feb. 2014.
M. E. van Raaij et al., "Concentration Dependence of α-Synuclein Fibril Length Assessed by Quantitative Atomic Force Microscopy and Statistical-Mechanical Theory", Biophysical Journal, vol. 95, Nov. 2008, pp. 4871-4878.
Examination Report issued in Canadian patent application No. 2,960,830, dated Jul. 16, 2019.
International Preliminary Report on Patentability issued in PCT Application No. PCT/US2018/032962, dated Nov. 22, 2019.
Final Office Action issued in U.S. Appl. No. 15/915,554 dated Nov. 22, 2019.
Non-Final Office Action issued in U.S. Appl. No. 16/233,848 dated Jan. 30, 2020.
Gonzalez-Montalban et al. "Highly Efficient Protein Misfolding Cyclic Amplification", PLoS Pathog. 2011 Fe; 7(2): e1001277 (Year: 2011).

(56) References Cited

OTHER PUBLICATIONS

International Search Report and Written Opinion Issued in PCT Application No. PCT/US2019/032749 dated Nov. 5, 2019.

Woerman et al. "Tau prions from Alzheimer's disease and chronic traumatic encephalopathy patients propagate in cultured cells," Proc Natl Acad Sci USA, Nov. 28, 2016 (Nov. 28, 2016), vol. 113, pp. E8187-E8196.

Saulle et al., "Chronic traumatic encephalopathy: a review," Rehabil Res Prac, Apr. 10, 2012, vol. 816069, pp. 1-10.

Edwards et al. "Amyloid-beta and tau pathology following repetitive mild traumatic brain injury, "Biochem Biophys Res Commun, Aug. 1, 2016, vol. 483, pp. 1137-1142.

Chen et al., "Estimating prion concentration in fluids and tissues by quantitative PMCA", Nature Methods, vol. 7 No. 7, Epub May 30, 2010.

Saá et al; "Ultra-efficient Replication of Infectious Prions by Automated Protein Misfolding Cyclic Amplification", J Biol Chemistry 281 (46): 35245-35252, Nov. 17, 2006, plus supplemental figure.

D'Castro, et al., "Isolation of Proteinase K-Sensitive Prions Using Pronase E and Phosphotungstic Acid" PLoS One, 2010, 5(12), e15679.

Onisko, et al., "Probing PrPSc Structure Using Chemical Cross-Linking and Mass Spectrometry: Evidence of the Proximity of Gly90 Amino Termini in the PrP 27-300 Aggregate" Biochemistry, 2005, 44, 10100-10109.

Deleault, et al., "Formation of native prions from minimal components in vitro." Proc. Nat. Acad. Sci. 2007, 104, 9741-9746.

Atarashi, et al., "Real-time quaking-induced conversion—A highly sensitive assay for prion detection." Prion 2011, 5(3), 150-153.

Makeig, "Response: Event-related brain dynamics—unifying brain electrophysiology" TINS, vol. 25, 2002, pp. 390-394.

Saborio et al., "Sensitive detection of pathological prion protein by cyclic amplification of protein misfolding", Nature, vol. 411, 2001, pp. 810-813.

Written Opinion issued in PCT application No. PCT/US2018/032962 dated Aug. 21, 2019.

Non-Final Office Action issued in U.S. Appl. No. 15/915,554 dated May 31, 2019.

Coalier KA et al. Stability of early-stage amyloid-beta (1-42) aggregation species. Biochimica et Biophysica Acta, 1834 (2013) 65-70.

Klunk WE et al. Quantifying amyloid by Congo Red spectral shift assays. Methods Enzymology, 309 (1999), 285-286. (Year: 1999).

Non-Final Office Action Issued in U.S. Appl. No. 15/981,449 dated Aug. 26, 2019.

Meyer "amplification of tau fibrils from minute quantites of seeds" Biochem 56:5804-5809 (Year: 2014).

Chen "Enhancement and destruction of antibody function by somatic mutation: unequal occurrence is controlled by V gene combinatorial associations" EMBO 14(12): 2784-2794 (year: 1995).

Non-Final Office Action issued in U.S. Appl. No. 16/414,749 dated Sep. 16, 2019.

Gill "acute plasma tau relates to prolonged return to play after concussion" neurology 88: 595-602 (Year: 2016).

Kanaan "Characterization of Early Pathological Tau Conformations and Phosphorylation in Chronic Traumatic Encephalopathy" J neuropath exp neurol 75(1): 19-34 (Year 2016).

Buée et al., "Tau protein isoforms, phosphorylation and role in neurodegenerative disorders", Brain Res Brain Res Rev. 33(1), p. 95-130 (2000).

Schmitz, et al. "The real-time quaking-induced conversion assay for detection of human prion disease and study of other protein misfolding diseases", Nat Protoc. Nov. 2016; 11(11):2233-2242.

\* cited by examiner

Table 1

| Antibodies (Company) | Epitope | Alpha-Synuclein oligomer capturing capacity |
|---|---|---|
| Alpha/beta-Synuclein Antibody N-19 (Santa Cruz Biotechnology) | N-terminal | +++ |
| Alpha-Synuclein Antibody C-20-R (Santa Cruz Biotechnology) | C-terminal | +++ |
| Alpha-Synuclein Antibody 211 (Santa Cruz Biotechnology) | Amino acids 121-125 | ++ |
| Alpha-synuclein Antibody Syn-204 (Santa Cruz Biotechnology) | Fragment 1-130 | + |
| 16 ADV Mouse IgG1 (Acumen) | Conformational | - |

+++  *Best*
++   *very good*
+    *good*
-    *no result*

DETECTION OF MISFOLDED ALPHA SYNUCLEIN PROTEIN

CROSS-REFERENCE TO RELATED APPLICATIONS

This application claims priority from U.S. Provisional Patent Application No. 62/049,304, filed on Sep. 11, 2014, the entire contents of which are incorporated herein by reference.

BACKGROUND

Protein misfolding disorders (PMDs) include Alzheimer's disease, Parkinson's disease, type 2 diabetes, Huntington's disease, amyotrophic lateral sclerosis, systemic amyloidosis, prion diseases, and the like. Misfolded aggregates of different proteins may be formed and accumulate. The misfolded aggregates may induce cellular dysfunction and tissue damage, among other effects.

For example, Parkinson's disease (PD) is a degenerative brain disorder with no effective treatment or accurate preclinical diagnosis. Evidence to date suggests that the misfolding, aggregation, and brain deposition of the alpha-synuclein protein (αS) may be triggering factors for PD pathology. Because the brain has low regeneration capacity, early diagnosis of PD is crucial to permit intervention before irreversible neuropathological changes occur. Several lines of evidence indicate that the process of αS misfolding and aggregation may begin years or decades before the onset of clinical symptoms and substantial brain damage. Current diagnosis of PD may include clinical examination complemented by imaging techniques used mainly to rule out other forms of dementia. Still, the lack of a widely accepted early, sensitive, and objective laboratory diagnosis remains a major problem for PD care.

The present application appreciates that diagnosis of PD may be a challenging endeavor.

SUMMARY

In one embodiment, a method for determining a presence of a soluble, misfolded αS protein in a sample is provided. The method may include contacting the sample with a monomeric, folded αS protein to form an incubation mixture. The method may include conducting an incubation cycle two or more times on the incubation mixture effective to form an amplified portion of misfolded αS protein from the monomeric, folded αS protein. Each incubation cycle may include incubating the incubation mixture effective to cause misfolding and/or aggregation of at least a portion of the monomeric, folded αS protein in the presence of the soluble, misfolded αS protein. Each incubation cycle may include physically disrupting the incubation mixture effective to at least partly de-aggregate at least a portion of a misfolded αS aggregate present, e.g., to release the soluble, misfolded αS protein. The method may include determining the presence of the soluble, misfolded αS protein in the sample by detecting at least a portion of the soluble, misfolded αS protein. The soluble, misfolded αS protein may include one or more of: a soluble, misfolded αS monomer and a soluble, misfolded αS aggregate. The amplified portion of misfolded αS protein may include one or more of: an amplified portion of the soluble, misfolded αS monomer, an amplified portion of the soluble, misfolded αS aggregate, and an insoluble, misfolded αS aggregate.

In another embodiment, a method for determining a presence of a soluble, misfolded αS protein in a sample is provided. The method may include contacting the sample with Thioflavin T and a molar excess of a monomeric, folded αS protein to form an incubation mixture. The molar excess may be greater than an amount of αS protein monomer included in the soluble, misfolded αS protein in the sample. The method may include conducting an incubation cycle two or more times to form the incubation mixture into a detection mixture. Each incubation cycle may include incubating the incubation mixture effective to cause misfolding and/or aggregation of at least a portion of the monomeric, folded αS protein in the presence of the soluble, misfolded αS protein to form an amplified portion of misfolded αS protein. Each incubation cycle may include shaking the incubation mixture effective to at least partly de-aggregate at least a portion of a misfolded αS aggregate present, e.g., to release the soluble, misfolded αS protein. The method may also include determining the presence of the soluble, misfolded αS protein in the sample by detecting a fluorescence of the Thioflavin T corresponding to soluble, misfolded αS protein. The soluble, misfolded αS protein may include one or more of: a soluble, misfolded αS monomer and a soluble, misfolded αS aggregate. The amplified portion of misfolded αS protein may include one or more of: an amplified portion of the soluble, misfolded αS monomer, an amplified portion of the soluble, misfolded αS aggregate, and an insoluble, misfolded αS aggregate.

In one embodiment, a method for determining a presence of a soluble, misfolded αS protein in a sample is provided. The method may include capturing soluble, misfolded αS protein from the sample. The method may include contacting the captured soluble, misfolded αS protein with a molar excess of monomeric, folded αS protein to form an incubation mixture. The molar excess may be greater than an amount of αS protein monomer included in the captured soluble, misfolded αS protein. The method may include conducting an incubation cycle two or more times to form the incubation mixture into a detection mixture. Each incubation cycle may include incubating the incubation mixture effective to cause misfolding and/or aggregation of at least a portion of the monomeric, folded αS protein in the presence of the captured soluble, misfolded αS protein to form an amplified portion of misfolded αS protein. Each incubation cycle may include physically disrupting the incubation mixture effective to at least partly de-aggregate at least a portion of a misfolded αS aggregate present, e.g., to release the soluble, misfolded αS protein. The method may also include determining the presence of the soluble, misfolded αS protein in the sample by detecting at least a portion of the soluble, misfolded αS protein. The soluble, misfolded αS protein may include one or more of: a soluble, misfolded αS monomer and a soluble, misfolded αS aggregate. The captured soluble, misfolded αS protein may include one or more of: a captured, soluble, misfolded αS monomer and a captured, soluble, misfolded αS aggregate. The amplified portion of misfolded αS protein may include one or more of: an amplified portion of the soluble, misfolded αS monomer, an amplified portion of the soluble, misfolded αS aggregate, and an insoluble, misfolded αS aggregate.

In another embodiment, a kit for determining a presence of a soluble, misfolded αS protein in a sample is provided. The kit may include one or more of a known amount of a monomeric, folded αS protein and a known amount of an indicator of misfolded αS protein. The kit may include instructions. The instructions may direct a user to contact the sample with one or more of the known amount of the monomeric, folded αS protein and the known amount of the indicator of misfolded αS protein to form an incubation mixture. The instructions may direct a user to repeat an incubation cycle two or more times to form the incubation mixture into a detection mixture. Each incubation cycle may include incubating the incubation mixture effective to cause misfolding and/or aggregation of at least a portion of the monomeric, folded αS protein in the presence of the soluble, misfolded αS protein to form an amplified portion of misfolded αS protein. Each incubation cycle may include physically disrupting the incubation mixture effective to at least partly de-aggregate at least a portion of a misfolded αS aggregate present, e.g., to release the soluble, misfolded αS protein. The instructions may direct a user to determine the presence of the soluble, misfolded αS protein in the sample by detecting the soluble, misfolded αS protein. The soluble, misfolded αS protein may include one or more of: a soluble, misfolded αS monomer and a soluble, misfolded αS aggregate. The amplified portion of misfolded αS protein may include one or more of: an amplified portion of the soluble, misfolded αS monomer, an amplified portion of the soluble, misfolded αS aggregate, and an insoluble, misfolded αS aggregate.

The methods and kits disclosed herein for determining a presence of a soluble, misfolded αS protein in a sample may be effective to determine an absence of the soluble, misfolded αS protein in the sample.

BRIEF DESCRIPTION OF THE DRAWINGS

The accompanying figures, which are incorporated in and constitute a part of the specification, illustrate example methods and results, and are used merely to illustrate example embodiments.

FIG. 3, Table 1 demonstrates the ability of different sequence or conformational antibodies to capture αS oligomers.

DETAILED DESCRIPTION

Figure 1A:
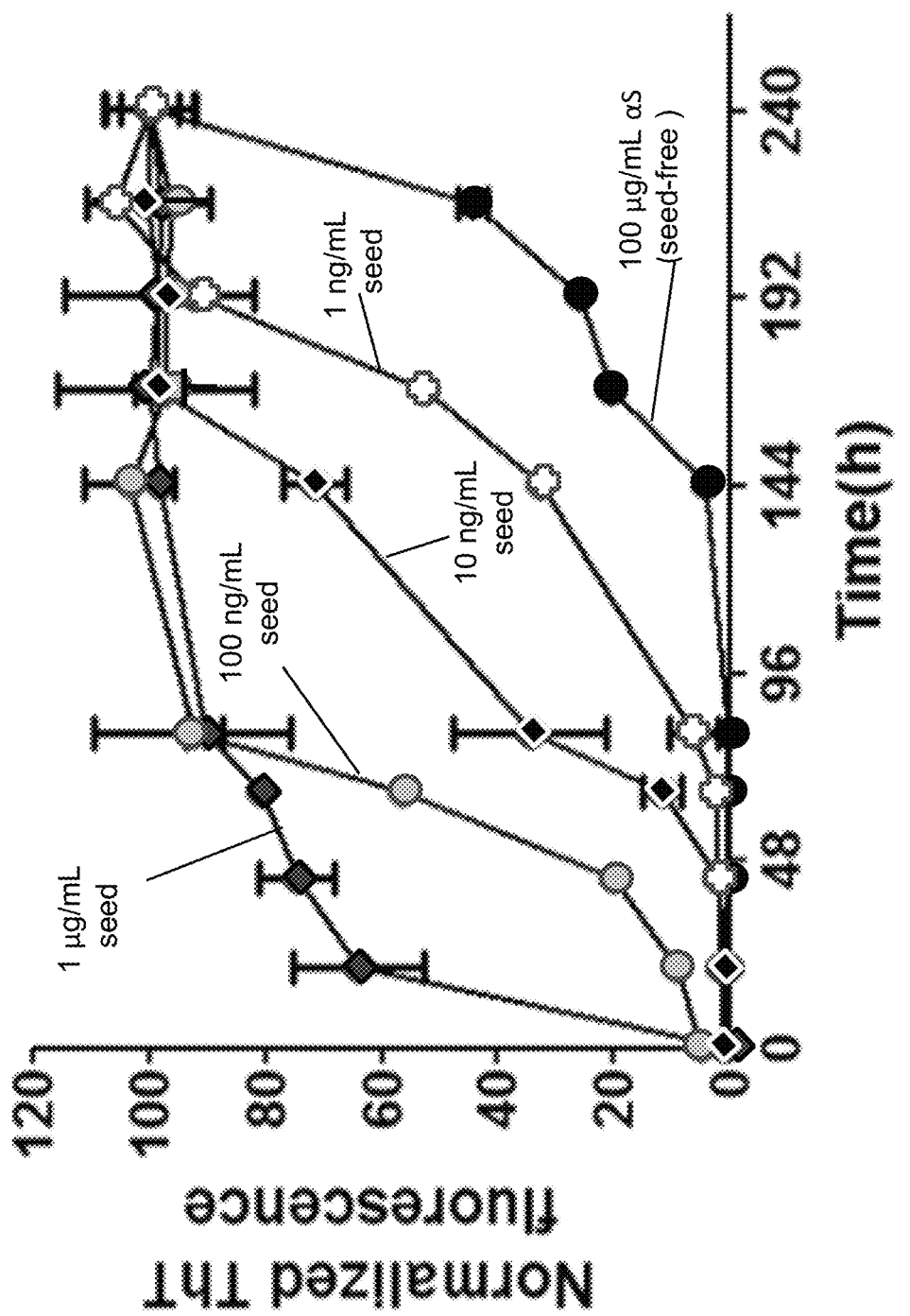
FIG. 1A is a graph of Thioflavin T fluorescence versus time showing the detection of αS seeds by PD-PMCA.

Methods and kits are provided for the detection of misfolded proteins, specifically misfolded αS in a sample, including for the diagnosis of PD and other disorders associated with αS misfolding, aggregation or deposition such as Multiple System Atrophy. This process, Protein Misfolding Cyclic Amplification (PMCA), may provide ultra-sensitive detection of misfolded aggregates through artificial acceleration and amplification of the misfolding and aggregation process in vitro. The basic concept of PMCA has been disclosed previously (Soto et al, WO 2002/04954; Estrada, et al. U.S. Pat. App. Pub. No. 20080118938, each of which is entirely incorporated herein by reference). However, prior to the present document, no patent publication has enabled PCMA for the amplification and detection of misfolded αS in a sample, including for the diagnosis of PD. This document discloses specific examples and details which enable PMCA technology for the detection of oligomeric αS proteins, as may be found in PD patients.

In various embodiments, methods for determining a presence of a soluble, misfolded αS protein in a sample are provided. As described herein, methods and kits for determining a presence of a soluble, misfolded αS protein in a sample may be effective to determine an absence of the soluble, misfolded αS protein in the sample. The soluble, misfolded αS protein described herein may be a pathogenic protein, e.g., causing or leading to various neural pathologies associated with PD or other disorders associated with αS misfolding, aggregation or deposition. The methods may include contacting the sample with a monomeric, folded αS protein to form an incubation mixture. The methods may include conducting an incubation cycle two or more times on the incubation mixture effective to form an amplified portion of misfolded αS protein from the monomeric, folded αS protein. Each incubation cycle may include incubating the incubation mixture effective to cause misfolding and/or aggregation of at least a portion of the monomeric, folded αS protein in the presence of the soluble, misfolded αS protein, e.g., to form an amplified portion of misfolded αS protein. Each incubation cycle may include physically disrupting the incubation mixture effective to at least partly de-aggregate at least a portion of a misfolded αS aggregate present e.g., to release the soluble, misfolded αS protein. The methods may include determining the presence of the soluble, misfolded αS protein in the sample by detecting at least a portion of the soluble, misfolded αS protein. The soluble, misfolded αS protein may include one or more of: a soluble, misfolded αS monomer and a soluble, misfolded αS aggregate. The amplified portion of misfolded αS protein may include one or more of: an amplified portion of the soluble, misfolded αS monomer, an amplified portion of the soluble, misfolded αS aggregate, and an insoluble, misfolded αS aggregate.

As used herein, "αS" or "alpha-synuclein" refers to full-length, 140 amino acid α-synuclein protein, e.g., "αS-140." Other isoforms or fragments may include "αS-126," alpha-synuclein-126, which lacks residues 41-54, e.g., due to loss of exon 3; and "αS-112" alpha-synuclein-112, which lacks residue 103-130, e.g., due to loss of exon 5. The αS may be present in brains of individuals suffering from PD or suspected of having PD. Various αS isoforms may include and are not limited to αS-140, αS-126, and αS-112. Various αS peptides may be associated with neuronal damage associated with PD.

As used herein, "monomeric, folded αS protein" refers to single αS protein molecules in their native, nonpathogenic, folded configuration. "Soluble, misfolded αS protein" refers to misfolded monomers or aggregates of αS protein that remain in solution. Examples of soluble, misfolded αS protein may include any number of aggregated misfolded αS protein monomers so long as the misfolded αS protein remains soluble. For example, soluble, misfolded αS protein may include aggregates of between 2 and about 50 units of misfolded αS protein monomer. In some examples, aggregates may be referred to as oligomers or polymers. In some examples, aggregation may be referred to as oligomerization or polymerization.

Soluble, misfolded αS protein may aggregate or oligomerize to form insoluble aggregates and/or higher oligomers, leading to αS protein aggregates in the form of protofibrils, fibrils, and eventually plaques or inclusion bodies. "Seeds" or "nuclei" refer to misfolded αS protein or short fragmented fibrils, particularly soluble, misfolded αS protein, with catalytic activity for inducing further misfolding, oligomerization, and/or aggregation. Such nucleation-dependent polymerization may be characterized by a slow lag phase wherein aggregated nuclei may form, which may then catalyze rapid formation of further and/or larger aggregates. The lag phase may be minimized or removed by addition of pre-formed nuclei or seeds. In some examples, "seeds" or "nuclei" may exclude unaggregated monomers of αS protein. Without wishing to be bound by theory, it is believed that at least under some conditions, monomeric, misfolded αS protein may not be stable, and the minimum stable size of pathogenic, misfolded αS protein may be an aggregate of two monomer units of misfolded αS protein.

As used herein, "soluble" species may form a solution in biological fluids under physiological conditions, whereas "insoluble" species may be present as precipitates, fibrils, deposits, tangles, or other non-dissolved forms in such biological fluids under physiological conditions. Such biological fluids may include, for example, fluids, or fluids expressed from one or more of: amniotic fluid; bile; blood; cerebrospinal fluid (CSF); cerumen; skin; exudate; feces; gastric fluid; lymph; milk; mucus, e.g. nasal secretions; mucosal membrane, e.g., nasal mucosal membrane; peritoneal fluid; plasma; pleural fluid; pus; saliva; sebum; semen; sweat; synovial fluid; tears; urine; and the like. Insoluble species may include, for example, fibrils of Aβ, αS, tau, and the like. A species that dissolves in a nonbiological fluid but not one of the aforementioned biological fluids under physiological conditions may be considered insoluble. For example, fibrils of αS and the like may be dissolved in a solution of, e.g., a surfactant such as sodium dodecyl sulfate (SDS) in water, but may still be insoluble in one or more of the mentioned biological fluids under physiological conditions.

In some embodiments, the sample may exclude insoluble species of the misfolded protein as a precipitate, fibril, deposit, tangle, plaque, or other form that may be insoluble in one or more of the described biological fluids under physiological conditions. The sample may exclude the misfolded αS protein in insoluble form, e.g., the sample may exclude the misfolded αS protein as a precipitate, fibril, deposit, tangle, plaque, or other insoluble form, e.g., in fibril form. The methods described herein may include preparing the sample by excluding the misfolded αS protein in insoluble form, e.g., by excluding from the sample the misfolded αS protein as a precipitate, fibril, deposit, tangle, plaque, or other insoluble form, e.g., in fibril form. The kits described herein may include instructions directing a user to prepare the sample by excluding the misfolded αS protein in insoluble form, e.g., by excluding from the sample the misfolded αS protein as a precipitate, fibril, deposit, tangle, plaque, or other insoluble form, e.g., in fibril form.

As used herein, aggregates of αS protein refer to non-covalent associations of protein including soluble, misfolded αS protein. Aggregates of αS protein may be "de-aggregated", broken up, or disrupted to release smaller aggregates, e.g., soluble, misfolded αS protein and fragmented fibrils. The catalytic activity of a collection of misfolded αS protein aggregate seeds may scale, at least in part with the number of seeds in a mixture. Accordingly, disruption of aggregates of αS protein in a mixture to release soluble, misfolded αS protein and fragmented fibrils seeds may lead to an increase in catalytic activity for aggregation of monomeric αS protein.

As used herein, a "misfolded protein" is a protein that no longer contains all or part of the structural conformation of the protein as it exists when involved in its typical, non-pathogenic normal function within a biological system. A misfolded protein may aggregate. A misfolded protein may localize in protein aggregate. A misfolded protein may be a non-functional protein. A misfolded protein may be a pathogenic conformer of the protein. Monomeric, folded αS protein compositions may be provided in native, nonpathogenic confirmations without the catalytic activity for misfolding, oligomerization, and aggregation associated with seeds. Monomeric, folded αS protein compositions may be provided in seed-free form.

In various embodiments, methods for determining a presence of a soluble, misfolded αS protein in a sample are provided. The methods may include contacting the sample with Thioflavin T and a molar excess of a monomeric, folded αS protein to form an incubation mixture. The molar excess may be greater than an amount of αS protein monomer included in the soluble, misfolded αS protein in the sample. The methods may include conducting an incubation cycle two or more times to form the incubation mixture into a detection mixture. Each incubation cycle may include incubating the incubation mixture effective to cause misfolding and/or aggregation of at least a portion of the monomeric, folded αS protein in the presence of the soluble, misfolded αS protein to form an amplified portion of misfolded αS protein. Each incubation cycle may include shaking the incubation mixture effective to at least partly de-aggregate at least a portion of a misfolded αS aggregate present, e.g., to release the soluble, misfolded αS protein. The methods may also include determining the presence of the soluble, misfolded αS protein in the sample by detecting a fluorescence of the Thioflavin T corresponding to soluble, misfolded αS protein. The soluble, misfolded αS protein may include one or more of: a soluble, misfolded αS monomer and a soluble, misfolded αS aggregate. The amplified portion of misfolded αS protein may include one or more of: an amplified portion of the soluble, misfolded αS monomer, an amplified portion of the soluble, misfolded αS aggregate, and an insoluble, misfolded αS aggregate.

In various embodiments, methods for determining a presence of a soluble, misfolded αS protein in a sample are provided. The methods may include capturing soluble, misfolded αS protein from the sample. The methods may include contacting the captured soluble, misfolded αS protein with a molar excess of monomeric, folded αS protein to form an incubation mixture. The molar excess may be greater than an amount of αS protein monomer included in the captured soluble, misfolded αS protein. The methods may include conducting an incubation cycle two or more times to form the incubation mixture into a detection mixture. Each incubation cycle may include incubating the incubation mixture effective to cause misfolding and/or aggregation of at least a portion of the monomeric, folded αS protein in the presence of the captured soluble, misfolded αS protein to form an amplified portion of misfolded αS protein. Each incubation cycle may include physically disrupting the incubation mixture effective to at least partly de-aggregate at least a portion of a misfolded αS aggregate present, e.g., to release the soluble, misfolded αS protein. The methods may also include determining the presence of the soluble, misfolded αS protein in the sample by detecting at least a portion of the soluble, misfolded αS protein. The soluble, misfolded αS protein may include one or more of: a soluble, misfolded αS monomer and a soluble, misfolded αS aggregate. The captured, soluble, misfolded αS protein may include one or more of: a captured, soluble, misfolded αS monomer and a captured, soluble, misfolded αS aggregate. The amplified portion of misfolded αS protein may include one or more of: an amplified portion of the soluble, misfolded αS monomer, an amplified portion of the soluble, misfolded αS aggregate, and an insoluble, misfolded αS aggregate.

As used herein, references to the soluble, misfolded αS protein may include any form of the soluble, misfolded αS protein, distributed in the sample, the incubation mixture, the detection mixture, and the like. For example, references to the soluble, misfolded αS protein may include the soluble, misfolded αS protein, for example, the soluble, misfolded αS protein in a sample from a subject suffering from PD. References to the soluble, misfolded αS protein may include, for example, the amplified portion of misfolded αS protein, e.g., in the incubation mixture and/or the detection mixture. References to the soluble, misfolded αS protein may include the captured soluble, misfolded αS protein, e.g., soluble, misfolded αS protein captured from the sample using αS specific antibodies.

In some embodiments, the methods may include contacting an indicator of misfolded αS protein to one or both of the incubation mixture or the detection mixture. The indicator of misfolded αS protein may be characterized by an indicating state in the presence of misfolded αS protein and a non-indicating state in the absence of misfolded αS protein. The determining the presence of the soluble, misfolded αS protein in the sample may include detecting the indicating state of the indicator of misfolded αS protein. The indicating state of the indicator and the non-indicating state of the indicator may be characterized by a difference in fluorescence, light absorption or radioactivity depending on the specific indicator. The determining the presence of the soluble, misfolded αS protein in the sample may include detecting the difference in fluorescence, light absorption or radioactivity depending on the specific indicator.

In several embodiments, the method may include contacting a molar excess of the indicator of misfolded αS protein to one or both of the incubation mixture or the detection mixture. The molar excess may be greater than a total molar amount of αS protein monomer included in the monomeric, folded αS protein and the soluble, misfolded αS protein in the one or both of the incubation mixture or the detection mixture.

In various embodiments, the indicator of misfolded αS protein may include one or more of: Thioflavin T, Congo Red, m-I-Stilbene, Chrysamine G, PIB, BF-227, X-34, TZDM, FDDNP, MeO-X-04, IMPY, NIAD-4, luminescent conjugated polythiophenes, a fusion with a fluorescent protein such as green fluorescent protein and yellow fluorescent protein, derivatives thereof, and the like.

In some embodiments, determining the presence of the soluble, misfolded αS protein in the sample may include determining an amount of the soluble, misfolded αS protein in the sample. The amount of the soluble, misfolded αS protein in the sample may be determined compared to a control sample. The amount of the soluble, misfolded αS protein in the sample may be detected with a sensitivity of at least about one or more of: 80%, 81%, 82%, 83%, 84%, 85%, 86%, 87%, 88%, 89%, 90%, 91%, 92%, 93%, 94%, 95%, 96%, 97%, 98%, 99%, and 100%. The amount of the soluble, misfolded αS protein in the sample detected may be less than about one or more of: 100 nmol, 10 nmol, 1 nmol, 100 pmol, 10 pmol, 1 pmol, 100 fmol, 10 fmol, 3 fmol, 1 fmol, 100 attomol, 10 attomol, and 1 attomol. The amount of the soluble, misfolded αS protein in the sample may be detected in a molar ratio to monomeric, folded αS protein comprised by the sample. The molar ratio may be less than about one or more of 1:100, 1:10,000, 1:100,000, and 1:1,000,000.

In various embodiments, the soluble, misfolded αS protein in the sample may be detected with a specificity of at least about one or more of: 80%, 81%, 82%, 83%, 84%, 85%, 86%, 87%, 88%, 89%, 90%, 91%, 92%, 93%, 94%, 95%, 96%, 97%, 98%, 99%, and 100%.

In some embodiments, the incubation mixture may include the monomeric, folded αS protein in a concentration, or in a concentration range, of one or more of: between about 1 nM and about 2 mM; between about 10 nM and about 200 µM; between about 100 nM and about 20 µM; or between about 1 µM and about 10 µM; and about 7 µM.

In several embodiments, the incubation mixture may include a buffer composition. The buffer composition may be effective to prepare or maintain the pH of the incubation mixture as described herein, e.g., between pH 5 and pH 9. The buffer composition may include one or more of: Tris-HCL, PBS, MES, PIPES, MOPS, BES, TES, and HEPES, and the like. The buffer concentration may be at a total concentration of between about 1 µm and about 1M. For example, the buffer may be Tris-HCL at a concentration of 0.1 M.

In various embodiments, the incubation mixture may include a salt composition. The salt composition may be effective to increase the ionic strength of the incubation mixture. The salt composition may include one or more of: NaCl, KCl, and the like. The incubation mixture may include the salt composition at a total concentration of between about 1 µm and about 500 mM.

In several embodiments, the incubation mixture may be characterized by, prepared with, or maintained at a pH value of or a pH range of one or more of: between about 5 and about 9; between about 6 and about 8.5; between about 7 and about 8; and about 7.4.

In some embodiments, the incubation mixture may be incubated at a temperature in ° C. of about one or more of: 4, 6, 8, 10, 12, 14, 16, 18, 20, 22, 24, 26, 28, 30, 32, 34, 35, 36, 37, 40, 45, 50, 55, and 60, e.g., about 22° C., or a temperature range between any two of the preceding values, for example, one or more of: between about 4° C. and about 60° C.; between about 4° C. and about 35° C.; between about 8° C. and about 50° C.; between about 12° C. and about 40° C.; between about 18° C. and about 30° C.; between about 18° C. and about 26° C.; and the like.

In several embodiments, the detecting the soluble, misfolded αS protein may include one or more of: a Western Blot assay, an enzyme-linked immunosorbent assay (ELISA), a thioflavin T binding assay, a Congo Red binding assay, a sedimentation assay, electron microscopy, atomic force microscopy, surface plasmon resonance, spectroscopy, and the like. The ELISA may include a two-sided sandwich ELISA. The spectroscopy may include one or more of: quasi-light scattering spectroscopy, multispectral ultraviolet spectroscopy, confocal dual-color fluorescence correlation spectroscopy, Fourier-transform infrared spectroscopy, capillary electrophoresis with spectroscopic detection, electron spin resonance spectroscopy, nuclear magnetic resonance spectroscopy, Fluorescence Resonance Energy Transfer (FRET) spectroscopy, and the like.

In various embodiments, the detecting the soluble, misfolded αS protein may include contacting the detection mixture with a protease. The soluble, misfolded αS protein may be detected using sequence-based or anti-misfolded protein antibodies in one or more of: a Western Blot assay and an ELISA.

In some embodiments, the method may include providing the monomeric, folded αS protein in labeled form. The monomeric, folded αS protein in labeled form may include one or more of: a covalently incorporated radioactive amino acid, a covalently incorporated, isotopically labeled amino acid, a covalently incorporated fluorophore, and the like. The detecting the soluble, misfolded αS protein may include detecting the monomeric, folded αS protein in labeled form as incorporated into the amplified portion of misfolded αS protein.

In several embodiments, the sample may be taken from a subject. The method may include determining or diagnosing the presence of PD in the subject according to the presence of the soluble, misfolded αS protein in the sample. The presence of the soluble, misfolded αS protein in the sample may be determined compared to a control sample taken from a control subject. The method may include determining or diagnosing the presence of a disease associated with alpha-synuclein homeostasis in the subject according to the presence of the soluble, misfolded αS protein in the sample. The method may include determining or diagnosing the presence of Multiple System Atrophy in the subject according to the presence of the soluble, misfolded αS protein in the sample.

In various embodiments, the detecting may include detecting an amount of the soluble, misfolded αS protein in the sample. The method may include determining or diagnosing the presence of PD in the subject by comparing the amount of the soluble, misfolded αS protein in the sample to a predetermined threshold amount.

In several embodiments, the sample may be taken from a subject exhibiting no clinical signs of dementia according to cognitive testing. The method may include determining or diagnosing the presence of PD in the subject according to the presence of the soluble, misfolded αS protein in the sample.

In various embodiments, the sample may be taken from a subject exhibiting clinical signs of dementia according to cognitive testing. The method may further include determining or diagnosing the presence of PD as a contributing factor to the clinical signs of dementia in the subject according to the presence of the soluble, misfolded αS protein in the sample.

In some embodiments, the sample may include one or more of: amniotic fluid; bile; blood; cerebrospinal fluid; cerumen; skin; exudate; feces; gastric fluid; lymph; milk; mucus, e.g. nasal secretions; mucosal membrane, e.g., nasal mucosal membrane; peritoneal fluid; plasma; pleural fluid; pus; saliva; sebum; semen; sweat; synovial fluid; tears; urine; and the like.

In several embodiments, the method may include taking the sample from the subject. The subject may be one of a: human, mouse, rat, dog, cat, cattle, horse, deer, elk, sheep, goat, pig, or non-human primate. Non-human animals may be wild or domesticated. The subject may be one or more of: at risk of PD, having PD, under treatment for PD; at risk of having a disease associated with dysregulation, misfolding, aggregation or disposition of αS; such as Multiple System Atrophy; having a disease associated with dysregulation, misfolding, aggregation or disposition of αS; under treatment for a disease associated with dysregulation, misfolding, aggregation or disposition of αS; and the like.

In various embodiments, the method may include determining or diagnosing a progression or homeostasis of PD in the subject by comparing the amount of the soluble, misfolded αS protein in the sample to an amount of the soluble, misfolded αS protein in a comparison sample taken from the subject at a different time compared to the sample.

For example, several novel therapeutics that are targeting αS homeostasis through various mechanisms are currently under development. Therapeutic approaches targeting αS homeostasis may include active immunization, such as PD01A+ or PD03A+, or passive immunization such as PRX002. A PMCA assay for αS oligomers may be employed to determine which patients may be treated with an αS modulating therapy. Patients showing a change, e.g., increase or decrease, in the level of αS oligomers as detected by the PMCA method may be classified as "responders" to αS modulating therapy, and may be treated with a therapeutic reducing the levels of αS oligomers. Patients lacking an aberrant αS homeostasis may be classified as "non responders" and may not be treated. Patients who could benefit from therapies aimed at modulating αS homeostasis may thus be identified.

Further, for example, the amount of αS oligomers may be measured in samples from patients using PMCA. Patients with elevated αS measurements may be treated with therapeutics modulating αS homeostasis. Patients with normal αS measurements may not be treated. A response of a patient to therapies aimed at modulating αS homeostasis may be followed. For example, αS oligomer levels may be measured in a patient sample at the beginning of a therapeutic intervention. Following treatment of the patient for a clinical meaningful period of time, another patient sample may be obtained and αS oligomer levels may be measured. Patients who show a change in αS levels following therapeutic intervention may be considered to respond to the treatment. Patients who show unchanged αS levels may be considered non-responding. The methods may include detection of αS aggregates in patient samples containing components that may interfere with the PMCA reaction.

In some embodiments, the subject may be treated with an αS modulating therapy. The method may include comparing the amount of the soluble, misfolded αS protein in the sample to an amount of the soluble, misfolded αS protein in a comparison sample. The sample and the comparison sample may be taken from the subject at different times over a period of time under the αS modulating therapy. The method may include determining or diagnosing the subject is one of: responsive to the αS modulating therapy according to a change in the soluble, misfolded αS protein over the period of time, or non-responsive to the αS modulating therapy according to homeostasis of the soluble, misfolded αS protein over the period of time. The method may include treating the subject determined to be responsive to the αS modulating therapy with the αS modulating therapy. The αS modulating therapy may include inhibiting the production of αS, inhibiting the aggregation of αS, e.g., with a suitable inhibitor, active or passive immunotherapy approaches, and the like.

In several embodiments, the amount of αS oligomers may be measured in samples from patients using PMCA. Patients with elevated αS measurements may be treated with disease modifying therapies for PD. Patients with normal αS measurements may not be treated. A response of a patient to disease-modifying therapies may be followed. For example, αS oligomer levels may be measured in a patient sample at the beginning of a therapeutic intervention. Following treatment of the patient for a clinical meaningful period of time, another patient sample may be obtained and αS oligomer levels may be measured. Patients who show a change in αS levels following therapeutic intervention may be considered to respond to the treatment. Patients who show unchanged αS levels may be considered non-responding. The method may include comparing the amount of the soluble, misfolded αS protein in the sample to an amount of the soluble, misfolded αS protein in a comparison sample. The sample and the comparison sample may be taken from the subject at different times over a period of time under the disease-modifying therapy for PD. The method may include determining the subject is one of: responsive to the disease-modifying therapy for PD according to a change in the soluble, misfolded αS protein over the period of time, or non-responsive to the disease-modifying therapy for PD according to homeostasis of the soluble, misfolded αS protein over the period of time. The method may include treating the subject determined to be responsive to the disease-modifying therapy for PD with the disease-modifying therapy for PD. Disease-modifying therapies of PD may include GDNF (Glia cell-line derived neurotrophic factor), inosine, Calcium-channel blockers, specifically Cav1.3 channel blockers such as isradipine, nicotine and nicotine-receptor agonists, GM-CSF, glutathione, PPAR-gamma agonists such as pioglitazone, and dopamine receptor agonists, including D2/D3 dopamine receptor agonists and LRRK2 (leucine-rich repeat kinase 2) inhibitors.

The methods may include detection of αS aggregates in patient samples containing components that may interfere with the PMCA reaction.

In several embodiments, the method may include selectively concentrating the soluble, misfolded αS protein in one or more of the sample, the incubation mixture, and the detection mixture. The selectively concentrating the soluble, misfolded αS protein may include pre-treating the sample prior to forming the incubation mixture. The selectively concentrating the soluble, misfolded αS protein may include pre-treating the incubation mixture prior to incubating the incubation mixture. The selectively concentrating the soluble, misfolded αS protein may include contacting one or more αS specific antibodies to the soluble, misfolded αS protein to form a captured soluble, misfolded αS protein. The one or more αS specific antibodies may include one or more of: α/β-synuclein N-19; α-synuclein C-20-R; α-synuclein 211; α-synuclein Syn 204; α-synuclein 2B2D1; α-synuclein LB 509; α-synuclein SPM451; α-synuclein 3G282; α-synuclein 3H2897; α/β-synuclein Syn 202; α/β-synuclein 3B6; α/β/γ-synuclein FL-140; and the like. The one or more αS specific antibodies may include one or more of: α/β-synuclein N-19; α-synuclein C-20-R; α-synuclein 211; α-synuclein Syn 204; and the like. Such antibodies may be obtained as follows: α/β-synuclein N-19 (cat. No. SC-7012, Santa Cruz Biotech, Dallas, Tex.); α-synuclein C-20-R (SC-7011-R); α-synuclein 211 (SC-12767); α-synuclein Syn 204 (SC-32280); α-synuclein 2B2D1 (SC-53955); α-synuclein LB 509 (SC-58480); α-synuclein SPM451 (SC-52979); α-synuclein 3G282 (SC-69978); α-synuclein 3H2897 (SC-69977); α/β-synuclein Syn 202 (SC-32281); α/β-synuclein 3B6 (SC-69699); and α/β/γ-synuclein FL-140 (SC-10717). The one or more αS specific antibodies may include one or more of: an antibody specific for an amino acid sequence of αS and an antibody specific for a conformation of the soluble, misfolded αS protein. The one or more αS specific antibodies may be coupled to a solid phase. The solid phase may include one or more of a magnetic bead and a multiwell plate.

For example, ELISA plates may be coated with the antibodies used to capture αS from the patient sample. The antibody-coated ELISA plates may be incubated with a patient sample, unbound materials may be washed off, and the PMCA reaction may be performed. Antibodies may also be coupled to beads. The beads may be incubated with the patient sample and used to separate αS-antibody complexes from the remainder of the patient sample.

In various embodiments, the contacting the sample with the monomeric, folded αS protein to form the incubation mixture may include contacting a molar excess of the monomeric, folded αS protein to the sample including the captured soluble, misfolded αS protein. The molar excess of the monomeric, folded αS protein may be greater than a total molar amount of αS protein monomer included in the captured soluble, misfolded αS protein. The incubating the incubation mixture may be effective to cause misfolding and/or aggregation of at least a portion of the monomeric, folded αS protein in the presence of the captured soluble, misfolded αS protein to form the amplified portion of misfolded αS protein.

In some embodiments, the protein aggregate may include one or more of: the monomeric, folded αS protein, the soluble, misfolded αS protein, and a captured form of the soluble, misfolded αS protein.

In several embodiments, the physically disrupting the incubation mixture may include one or more of: sonication, stirring, shaking, freezing/thawing, laser irradiation, autoclave incubation, high pressure, homogenization, and the like. For example, shaking may include cyclic agitation. The cyclic agitation may be conducted between about 50 rotations per minute (RPM) and 10,000 RPM. The cyclic agitation may be conducted between about 200 RPM and about 2000 RPM. The cyclic agitation may be conducted at about 500 RPM.

In various embodiments, the physically disrupting the incubation mixture may be conducted in each incubation cycle for between about 5 seconds and about 10 minutes, between about 30 sec and about 1 minute, between about 45 sec and about 1 minute, for about 1 minute, and the like. For example, the physically disrupting the incubation mixture may be conducted in each incubation cycle by shaking for one or more of: between about 5 seconds and about 10 minutes, between about 30 sec and about 1 minute, between about 45 sec and about 1 minute, for about 1 minute, and the like. The incubating the incubation mixture may be independently conducted, in each incubation cycle, for a time between about 1 minute and about 5 hours, between about 10 minutes and about 2 hours, between about 15 minutes and about 1 hour, between about 25 minutes and about 45 minutes, and the like. Each incubation cycle may include independently incubating and physically disrupting the incubation mixture for one or more of: incubating between about 1 minute and about 5 hours and physically disrupting between about 5 seconds and about 10 minutes; incubating between about 10 minutes and about 2 hours and physically disrupting between about 30 sec and about 1 minute; incubating between about 15 minutes and about 1 hour and physically disrupting between about 45 sec and about 1 minute; incubating between about 25 minutes and about 45 minutes and physically disrupting between about 45 sec and about 1 minute; and incubating about 1 minute and physically disrupting about 1 minute.

The conducting the incubation cycle may be repeated between about 2 times and about 1000 times, between about 5 times and about 500 times, between about 50 times and about 500 times, between about 150 times and about 250 times, and the like. The incubating the incubation mixture being independently conducted, in each incubation cycle, at a temperature in ° C. of about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or a range between any two of the preceding values, for example, between about 15° C. and about 50° C.

In several embodiments, contacting the sample with the monomeric, folded αS protein to form the incubation mixture may be conducted under physiological conditions. Contacting the sample with the monomeric, folded αS protein to form the incubation mixture may include contacting the sample with a molar excess of the monomeric, folded αS protein. The molar excess may be greater than a total molar amount of αS protein monomer included in the soluble, misfolded αS protein in the sample. The monomeric, folded αS protein and/or the soluble, misfolded αS protein may include one or more peptides formed via proteolytic cleavage of αS-140. The monomeric, folded αS protein and/or the soluble, misfolded αS protein may include one or more of: αS-140, αS-126, αS-112, and the like. As used herein, "αS-140" refers to full-length, 140 amino acid α-synuclein protein. Other isoforms may include "αS-126," alpha-synuclein-126, which lacks residues 41-54, e.g., due to loss of exon 3; and "αS-112" alpha-synuclein-112, which lacks residue 103-130, e.g., due to loss of exon 5.

In various embodiments of the methods described herein, the soluble, misfolded αS protein may substantially be the soluble, misfolded αS aggregate. The amplified portion of misfolded αS protein may substantially be one or more of: the amplified portion of the soluble, misfolded αS aggregate and the insoluble, misfolded αS aggregate. The monomeric, folded αS protein may be produced by one of: chemical synthesis, recombinant production, or extraction from non-recombinant biological samples.

In various embodiments, kits for determining a presence of a soluble, misfolded αS protein in a sample are provided. The kits may include one or more of a known amount of a monomeric, folded αS protein and a known amount of an indicator of the soluble, misfolded αS protein. The kits may include instructions. The instructions may direct a user to conduct any of the methods described herein. For example, the instructions may direct the user to contact the sample with one or more of the known amount of the monomeric, folded αS protein and the known amount of the indicator of misfolded αS protein to form an incubation mixture. The instructions may direct a user to repeat an incubation cycle two or more times to form the incubation mixture into a detection mixture. Each incubation cycle may include incubating the incubation mixture effective to cause misfolding and/or aggregation of at least a portion of the monomeric, folded αS protein in the presence of the soluble, misfolded αS protein to form an amplified portion of misfolded αS protein. Each incubation cycle may include physically disrupting the incubation mixture effective to at least partly de-aggregate at least a portion of a misfolded αS aggregate present, e.g., to release the soluble, misfolded αS protein. The instructions may direct a user to determine the presence of the soluble, misfolded αS protein in the sample by detecting the soluble, misfolded αS protein. The soluble, misfolded αS protein may include one or more of: a soluble, misfolded αS monomer and a soluble, misfolded αS aggregate. The amplified portion of misfolded αS protein may include one or more of: an amplified portion of the soluble, misfolded αS monomer, an amplified portion of the soluble, misfolded αS aggregate, and an insoluble, misfolded αS aggregate.

In various embodiments, the kit may include the known amount of the monomeric, folded αS protein and the known amount of the indicator of misfolded αS protein. The kit may include one or more of: a multiwall microtitre plate; a microfluidic plate; a shaking apparatus; an incubating apparatus; and a fluorescence measurement apparatus; included either as one or more of the individual plates or apparatuses, or as a combination device. For example, a shaking microplate reader may be used to perform cycles of incubation and shaking and automatically measure the ThT fluorescence emission during the course of an experiment (e.g., FLUOstar OPTIMA, BMG LABTECH Inc., Cary, N.C.).

In several embodiments of the kit, an indicating state and a non-indicating state of the indicator of misfolded αS protein may be characterized by a difference in fluorescence, light absorption or radioactivity depending on the specific indicator. The instructions may direct the user to determine the presence of the soluble, misfolded αS protein in the sample by fluorescence spectroscopy, light absorption or radioactivity depending on the specific indicator.

In some embodiments of the kit, the indicator of misfolded αS protein may include one or more of: Thioflavin T, Congo Red, m-I-Stilbene, Chrysamine G, PIB, BF-227, X-34, TZDM, FDDNP, MeO-X-04, IMPY, NIAD-4, luminescent conjugated polythiophenes, a fusion with a fluorescent protein such as green fluorescent protein and yellow fluorescent protein, derivatives thereof, and the like. The monomeric, folded αS protein may include one or more of a covalently incorporated radioactive amino acid, a covalently incorporated, isotopically labeled amino acid, and a covalently incorporated fluorophore.

In various embodiments of the kit, the instructions may direct a user to conduct any of the methods described herein. For example, the instructions may include directions to the user to determine an amount of the soluble, misfolded αS protein in the sample. The instructions may direct the user to detect the soluble, misfolded αS protein by conducting one or more of: a Western Blot assay, an enzyme-linked immunosorbent assay (ELISA), a thioflavin T binding assay, a Congo Red binding assay, a sedimentation assay, electron microscopy, atomic force microscopy, surface plasmon resonance, spectroscopy, and the like.

The instructions may direct the user to detect the soluble, misfolded αS protein by contacting the detection mixture with a protease; and detecting the soluble, misfolded αS protein using sequence-based or anti-misfolded protein antibodies in one or more of: a Western Blot assay and an ELISA.

In several embodiments of the kit, the instructions may direct the user to take the sample from a subject. The instructions may include directing the user to determine the presence of PD in the subject according to the presence of the soluble, misfolded αS protein in the sample. The presence of the soluble, misfolded αS protein in the sample may be determined compared to a control sample taken from a control subject. The instructions may direct the user to determine the presence of PD in the subject by comparing the amount of the soluble, misfolded αS protein in the sample to a predetermined threshold amount. The instructions may direct the user to obtain the sample including one or more of: amniotic fluid; bile; blood; cerebrospinal fluid; cerumen; skin; exudate; feces; gastric fluid; lymph; milk; mucus, e.g. nasal secretions; mucosal membrane, e.g., nasal mucosal membrane; peritoneal fluid; plasma; pleural fluid; pus; saliva; sebum; semen; sweat; synovial fluid; tears; urine; and the like. The instructions may direct the user to determine a progression or homeostasis of PD in the subject by comparing the amount of the soluble, misfolded αS protein in the sample to an amount of the soluble, misfolded αS protein in a comparison sample taken from the subject at a different time compared to the sample.

The instructions may direct the user to the user to selectively concentrate the soluble, misfolded αS protein in one or more of the sample, the incubation mixture, and the detection mixture. For example, the kit may include one or more αS specific antibodies configured to selectively concentrate or capture the soluble, misfolded αS protein. The one or more αS specific antibodies may include one or more of: an antibody specific for an amino acid sequence of αS and an antibody specific for a conformation of the soluble, misfolded αS protein. The one or more αS specific antibodies may include one or more of: α/β-synuclein N-19; α-synuclein C-20-R; α-synuclein 211; α-synuclein Syn 204; α-synuclein 2B2D1; α-synuclein LB 509; α-synuclein SPM451; α-synuclein 3G282; α-synuclein 3H2897; α/β-synuclein Syn 202; α/β-synuclein 3B6; α/β/γ-synuclein FL-140; and the like. The one or more αS specific antibodies may include one or more of: α/β-synuclein N-19; α-synuclein C-20-R; α-synuclein 211; α-synuclein Syn 204; and the like. The instructions may direct the user to selectively concentrate the soluble, misfolded αS protein by contacting the one or more αS specific antibodies to the soluble, misfolded αS protein to form a captured soluble, misfolded αS protein. The one or more αS specific antibodies may be provided coupled to a solid phase. The solid phase may include one or more of a magnetic bead or a multiwell plate.

In various embodiments of the kit, the instructions for physically disrupting the incubation mixture may direct the user to employ one or more of: sonication, stirring, shaking, freezing/thawing, laser irradiation, autoclave incubation, high pressure, homogenization, and the like. The instructions may direct the user to conduct cyclic agitation according to any RPM range described herein, for example, between about 50 RPM and 10,000 RPM. The instructions may direct the user to conduct the physical disruption in each incubation cycle according to any time range described herein, for example, between about 5 seconds and about 10 minutes. The instructions may direct the user to incubate the incubation mixture in each incubation cycle according to any time range described herein, for example, for a time between about 1 minute and about 5 hours. The instructions for conducting the incubation cycle may direct the user to repeat the incubation cycle for any number of repetitions described herein, for example, between about 2 times and about 1000 times. Instructions for conducting the incubation cycle may include directions to a user to incubate at a temperature between about 15° C. and about 50° C.

In various embodiments of the kits described herein, the soluble, misfolded αS protein may substantially be the soluble, misfolded αS aggregate. The amplified portion of misfolded αS protein may substantially be one or more of: the amplified portion of the soluble, misfolded αS aggregate and the insoluble, misfolded αS aggregate. The monomeric, folded αS protein may be produced by one of: chemical synthesis, recombinant production, or extraction from non-recombinant biological samples.

EXAMPLES

Example 1

Detection of αS Seeds by PD-PMCA

Example 1A

Seeding of αS aggregation was studied by incubating a solution of seed-free αS in the presence of Thioflavin T with or without different quantities of synthetic soluble, misfolded αS protein: Control (no αS oligomer); or 1 ng/mL, 10 ng/mL, 100 ng/mL, and 1 μg/mL of the synthetic soluble, misfolded αS protein seed. αS-PMCA general procedure: Solutions of 100 μg/mL αS seed-free αS in PBS, pH 7.4 (200 μL total volume) were placed in opaque 96-wells plates and incubated alone or in the presence of the indicated concentrations of synthetic αS aggregates or 40 μL of CSF aliquots. Samples were incubated in the presence of 5 μM Thioflavin T (ThT) and subjected to cyclic agitation (1 min at 500 rpm followed by 29 min without shaking) using an Eppendorf thermomixer, at a constant temperature of 22° C. At various time points, ThT fluorescence was measured in the plates at 485 nm after excitation at 435 nm using a plate spectrofluorometer. FIG. 1A is a graph of Thioflavin T fluorescence as a function of time, showing the detection of αS seeds by PD-PMCA, using the indicated concentration of synthetic soluble, misfolded αS protein seeds. The peptide concentration, temperature and pH of the buffer were monitored to control the extent of the lag phase and reproducibility among experiments. Aggregation of monomeric, folded αS protein was observed in the presence of 1 ng/mL, 10 ng/mL, 100 ng/mL, and 1 μg/mL αS of the synthetic soluble, misfolded αS protein seed.

Example 1B

Figure 1B:
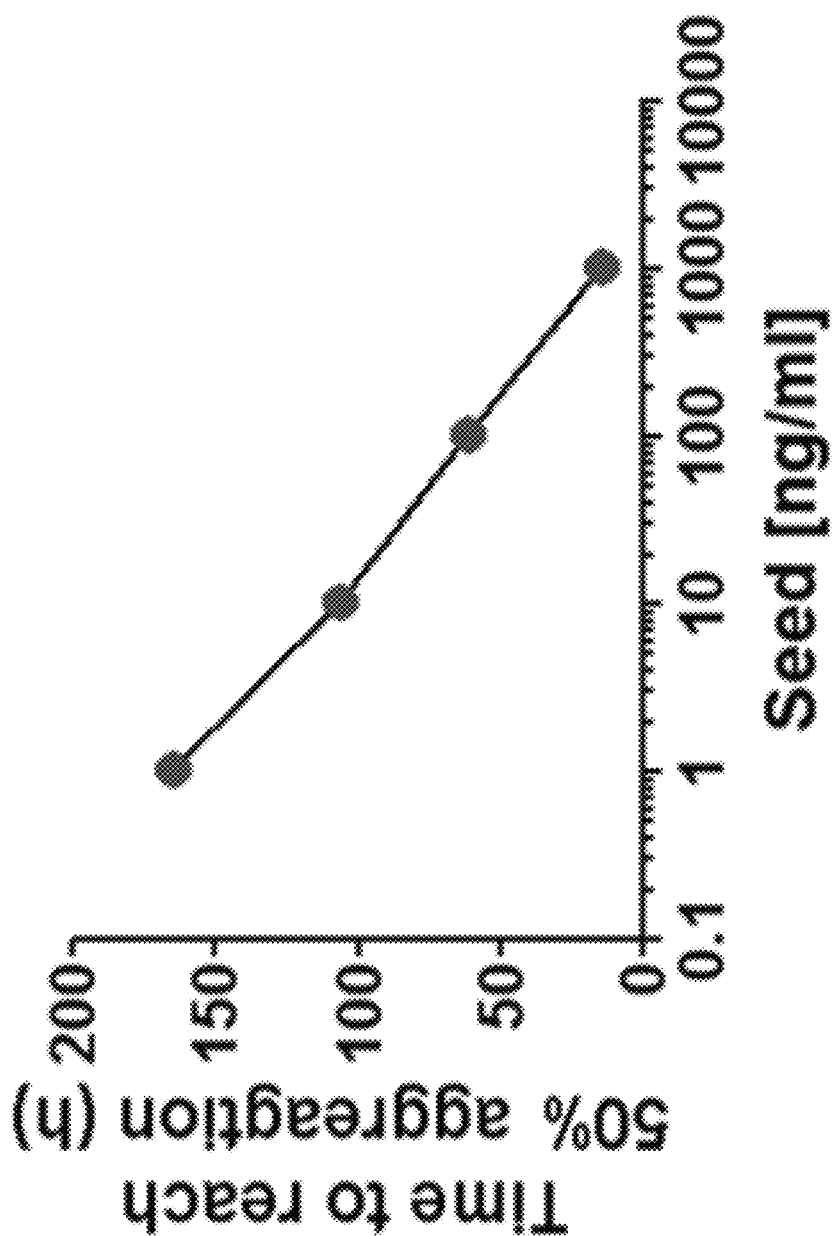
FIG. 1B is a graph of time to reach 50% aggregation plotted as a function of the indicated amounts αS seeds.

The time to reach 50% aggregation as a function of amounts of αS seeds added was determined using the samples in EXAMPLE 1A. FIG. 1B is a graph showing time to reach 50% aggregation plotted as a function of amounts of αS seeds added.

Example 2

αS-PMCA Detects Oligomeric αS in the Cerebrospinal Fluid of PD Patients

Figure 2:
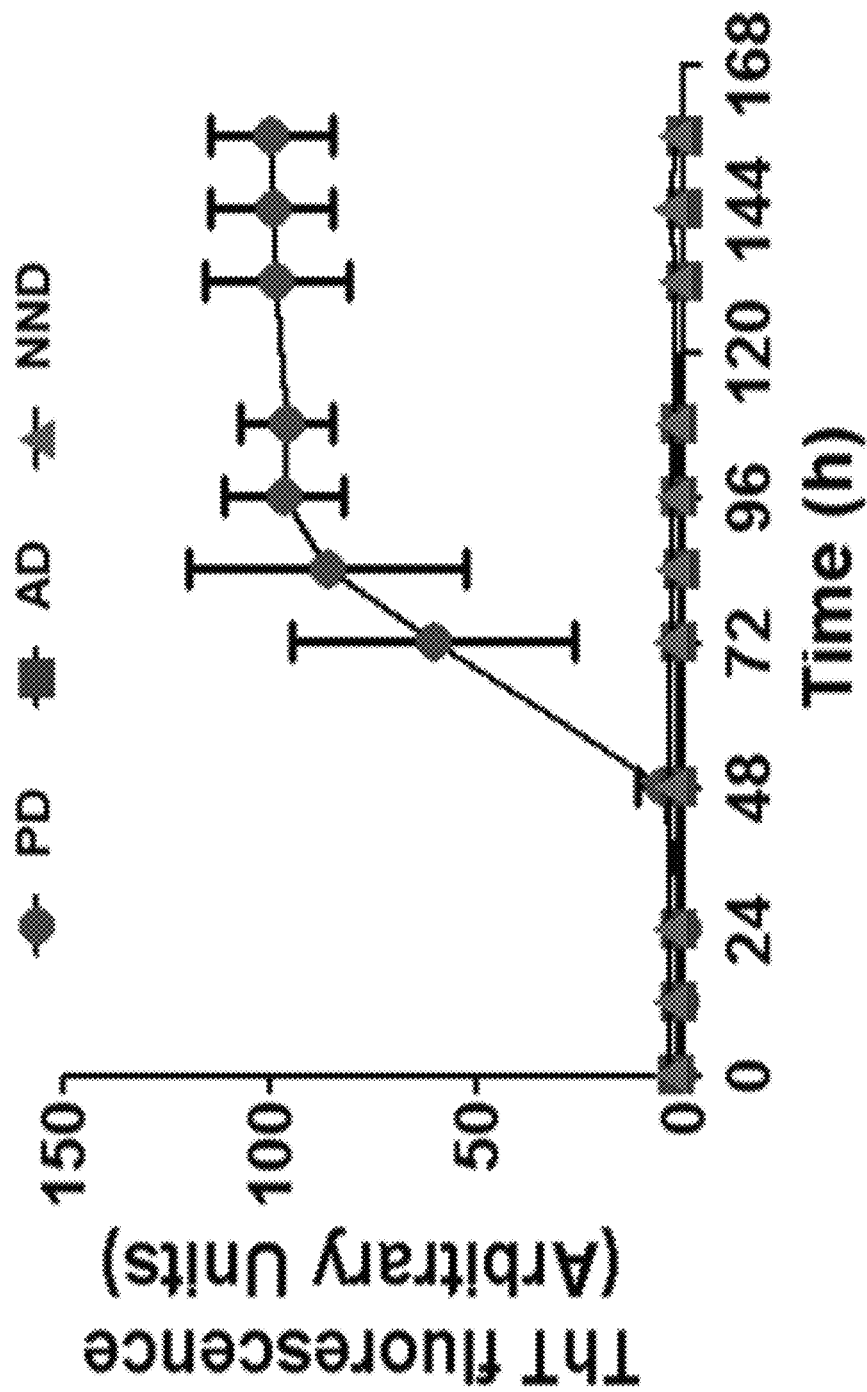
FIG. 2 shows detection of αS seeds in CSF samples from human PD patients by PD-PMCA, versus controls with Alzheimer's disease (AD) or a non-neurodegenerative disease (NND).

FIG. 2 shows detection of seeding activity in human CSF samples from controls and PD patients by PD-PMCA. Purified seed free alpha-synuclein (100 μg/mL) in PBS, pH 7.4 was allowed to aggregate at 37° C. with shaking at 500 rpm in the presence of CSF from human patients with confirmed PD, AD or non-neurodegenerative neurological diseases (NND). The extend of aggregation was monitored by Thioflavin fluorescence at 485 nm after excitation at 435 nm using a plate spectrofluorometer.

Aliquots of CSF were obtained from PD patients, cognitively normal individuals affected by non-degenerative neurological diseases (NND), and patients affected by Alzheimer's disease (AD). Test CSF samples were obtained from patients with the diagnosis of probable PD as defined by the DSM-IV and determined using a variety of tests, including routine medical examination, neurological evaluation, neuropsychological assessment, and magnetic resonance imaging. CSF samples were collected in polypropylene tubes following lumbar puncture at the L4/L5 or L3/L4 interspace with atraumatic needles after one night fasting. The samples were centrifuged at 3,000 g for 3 min at 4° C., aliquoted and stored at −80° C. until analysis. CSF cell counts, glucose and protein concentration were determined. Albumin was measured by rate nephelometry. To evaluate the integrity of the blood brain barrier and the intrathecal IgG production, the albumin quotient (CSF albumin/serum albumin)×$10^3$ and the IgG index (CSF albumin/serum albumin)/(CSF IgG/serum IgG) were calculated. The study was conducted according to the provisions of the Helsinki Declaration and was approved by the Ethics Committee.

The experiments as well as the initial part of the analysis were conducted blind. FIG. 2 is a graph of αS misfolding and/or aggregation versus time, measured as a function of ThT fluorescence labeling, showing the average kinetics of αS aggregation of representative samples from the PD, AD, and NND groups.

The results indicate that CSF from PD patients significantly accelerates αS aggregation as compared to control CSF ($P<0.001$). The significance of the differences in αS aggregation kinetics in the presence of human CSF samples was analyzed by one-way ANOVA, followed by the Tukey's multiple comparison post-test. The level of significance was set at $P<0.05$. The differences between PD and samples from the other two groups were highly significant with $P<0.001$ (***).

Example 3

Specificity of Immuno Capturing

FIG. 3 shows Table 1, demonstrating the ability of different sequence or conformational antibodies to capture αS oligomers. The capacity to capture oligomers was measured by spiking synthetic αS oligomers in healthy human blood plasma and detection by αS-PMCA. The first column shows various antibodies tested and corresponding commercial sources. The second column lists the epitope recognition site on the αS protein of the diverse sequence antibodies used in this study. The third column indicates the observed ability of specific antibodies to capture the αS oligomers. The symbols indicate that the detection limits using the different antibodies were: <12 fmol (+++); between 10-100 fmol (++); >1 pmol (+) and not significantly higher than without capturing reagent (−). Alpha/beta-synuclein antibody N-19 (N-terminal epitope) and alpha-synuclein antibody C-20-R (C-terminal epitope) showed the best results; and alpha-synuclein antibody 211 (epitope: amino acids 121-125) showed very good results; alpha-synuclein antibody 204 (epitope: fragment 1-130) showed good results; and 16 ADV Mouse IgG1 (conformational epitope) showed no result.

Example 4

Solid Phase Immuno Capturing

Figure 4A:
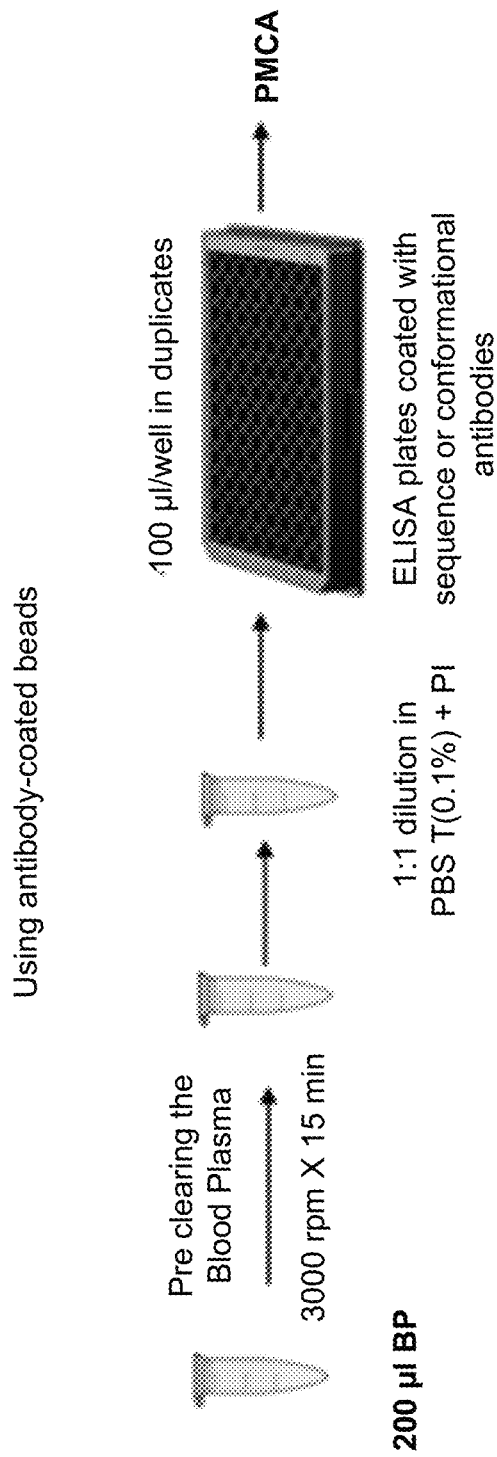
FIG. 4A is a schematic representation of an ELISA solid phase method employed to capture αS oligomers.
Figure 4B:
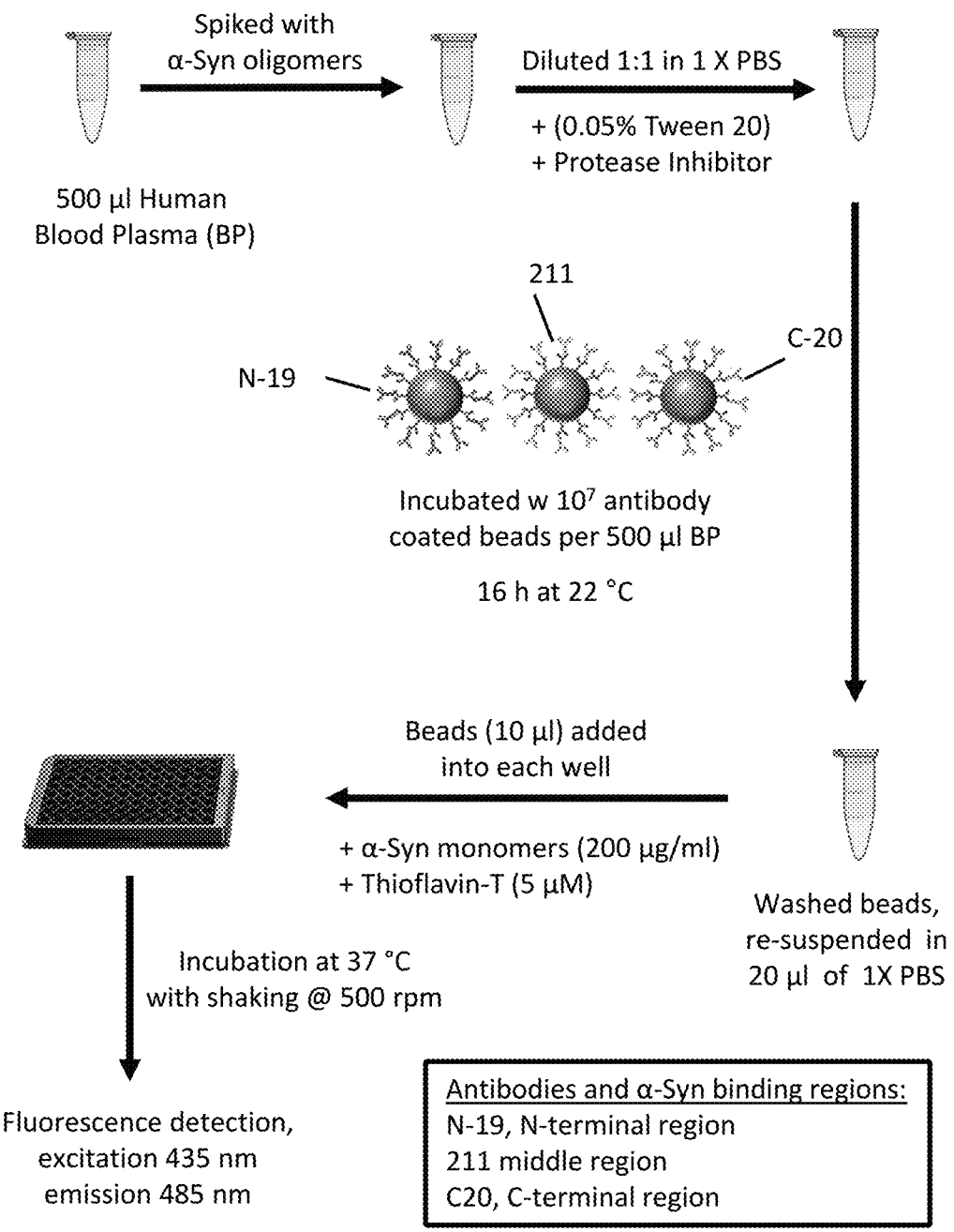
FIG. 4B is a schematic representation of a magnetic bead solid phase method employed to capture αS oligomers.

FIGS. 4A and 4B are schematic representations of two solid phase methods used to capture soluble, misfolded αS protein from complex samples such as blood plasma. Strategy 1 employed ELISA plates pre-coated with specific antibodies bound to a solid phase on the ELISA plate. After washing the plates, the αS-PMCA reaction was carried out in the same plates. Strategy 2 used magnetic beads as the solid phase coated with specific antibodies. This approach provided concentration of the samples.

Example 5

αS-PMCA for the Detection of α-Synuclein Oligomers Spiked in Human Blood Plasma

Figure 5A:
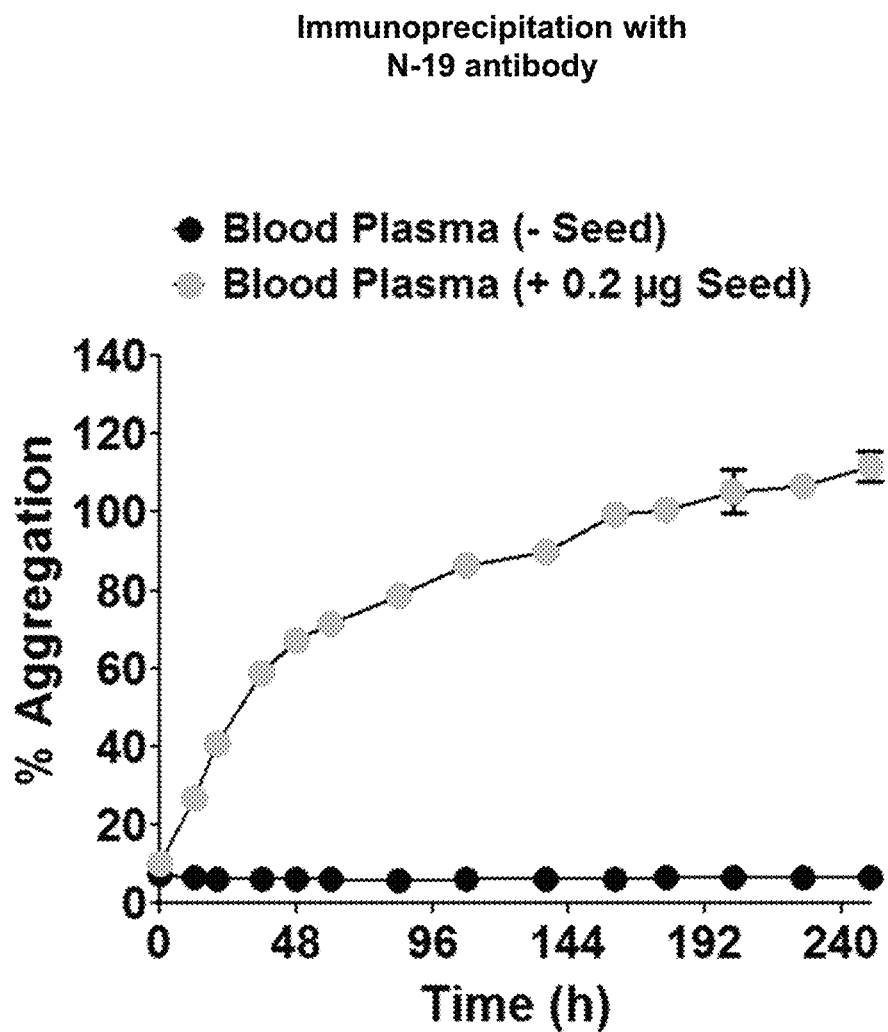
FIG. 5A is a graph that shows the results of immunoprecipitation/aggregation of αS oligomers from human blood plasma using a N-19 αS antibody.
Figure 5B:
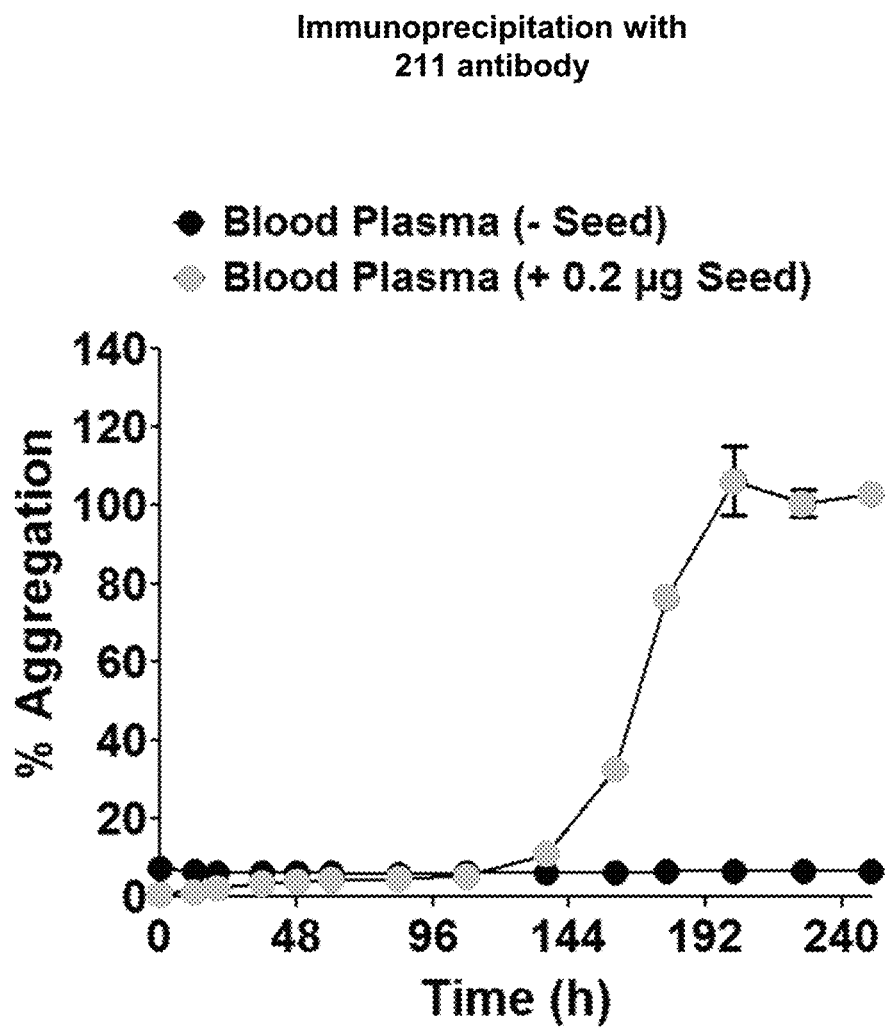
FIG. 5B is a graph that shows the results of immunoprecipitation/aggregation of αS oligomers from human blood plasma using a 211 αS antibody.
Figure 5C:
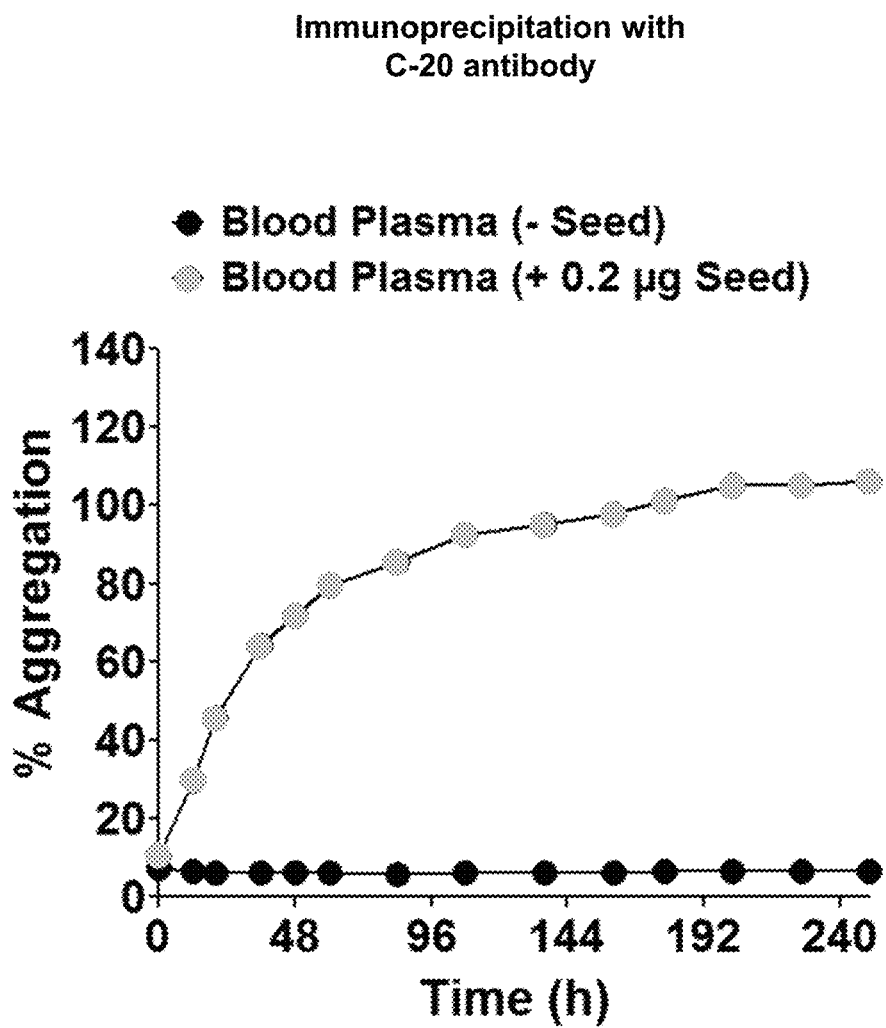
FIG. 5C is a graph that shows the results of immunoprecipitation/aggregation of αS oligomers from human blood plasma using a C-20 αS antibody.

Immunoprecipitation of α-Synuclein oligomers from human blood plasma was performed by anti-α-Synuclein antibody-coated beads (Dynabeads) and a seeding aggregation assay using α-Synuclein monomers as seeding substrate along with thioflavin-T for detection. The anti-α-Synuclein coated beads ($1\times10^7$ beads) were incubated with human blood plasma (500 μL) with α-Synuclein seeds (+0.2 μg Seed) and without α-Synuclein seeds (− Seed). After immunoprecipitation, the beads were re-suspended in 20 μL of reaction buffer (1×PBS), and 10 μL of beads were added to each well of a 96-well plate. The aggregation assay was performed by adding α-Synuclein monomers (200 μg/mL) and thioflavin-T (5 μM). The increase in florescence was monitored by a fluorimeter using an excitation of 435 nm and emission of 485 nm. FIG. 5A illustrates immunoprecipitation/aggregation results with N-19 antibody in blood plasmas with and without seed. FIG. 5B illustrates immunoprecipitation/aggregation results with 211 antibody in blood plasmas with and without seed. FIG. 5C illustrates immunoprecipitation/aggregation results with C-20 antibody in blood plasmas with and without seed.

Figure 6A:
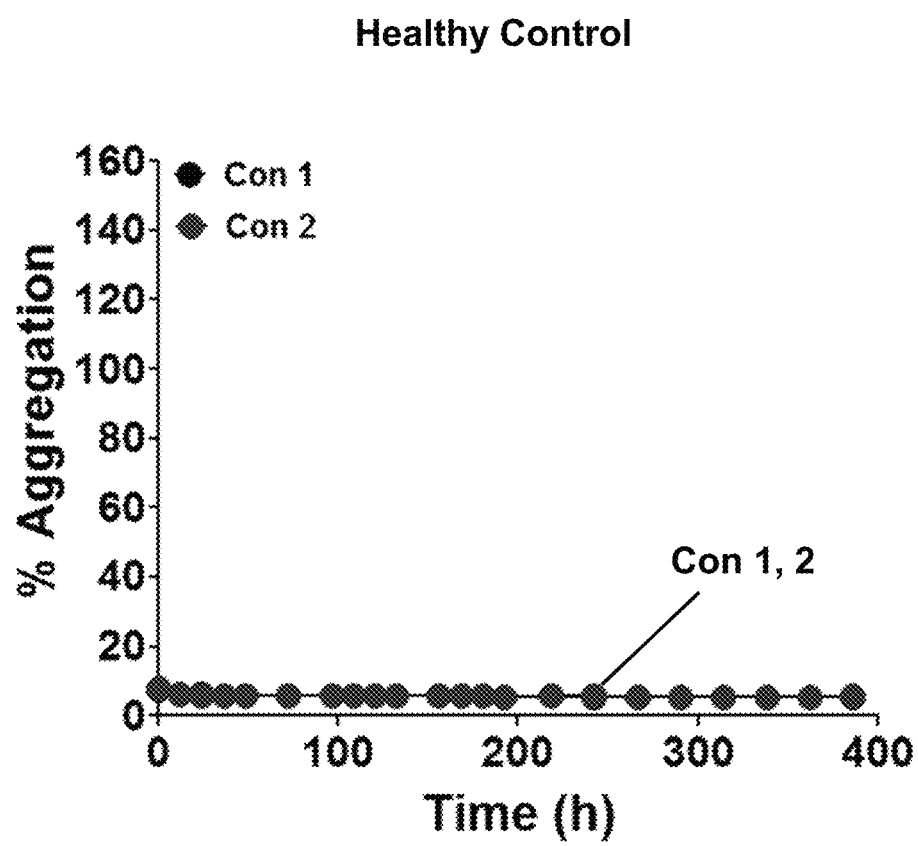
FIG. 6A is a graph that shows the results in control samples for the detection of αS seeds in CSF samples.
Figure 6B:
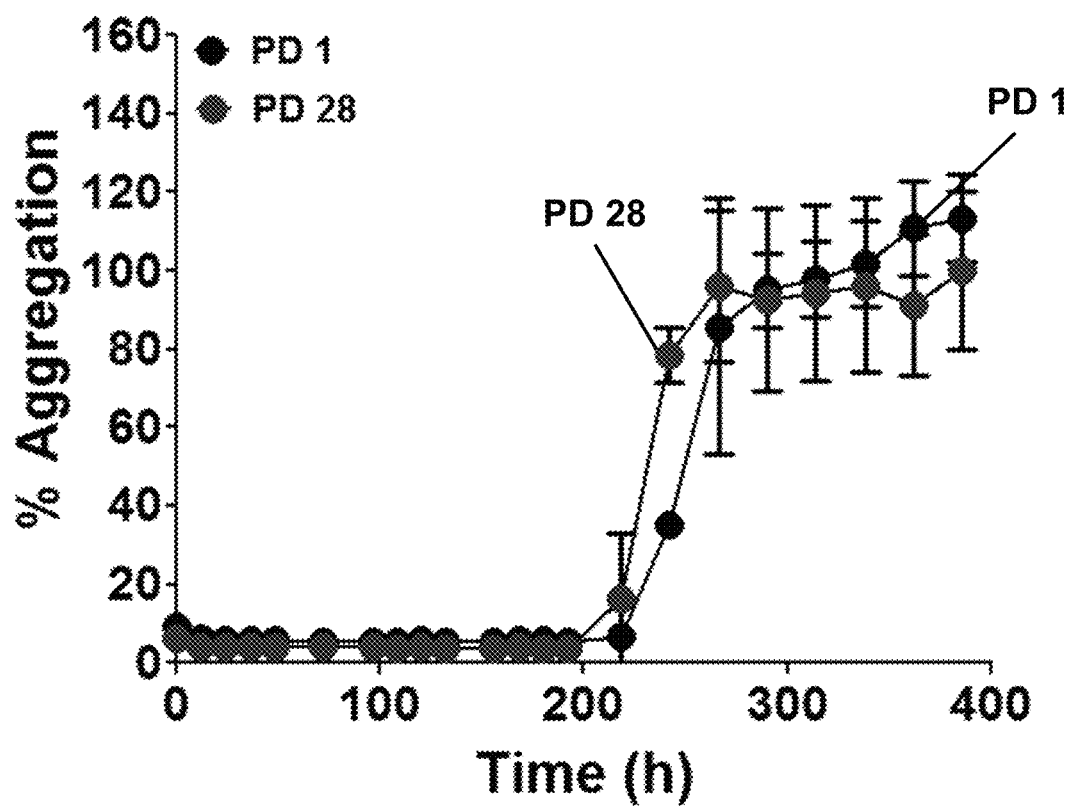
FIG. 6B is a graph that shows the results in PD patients for the detection of αS seeds in CSF samples.
Figure 6C:
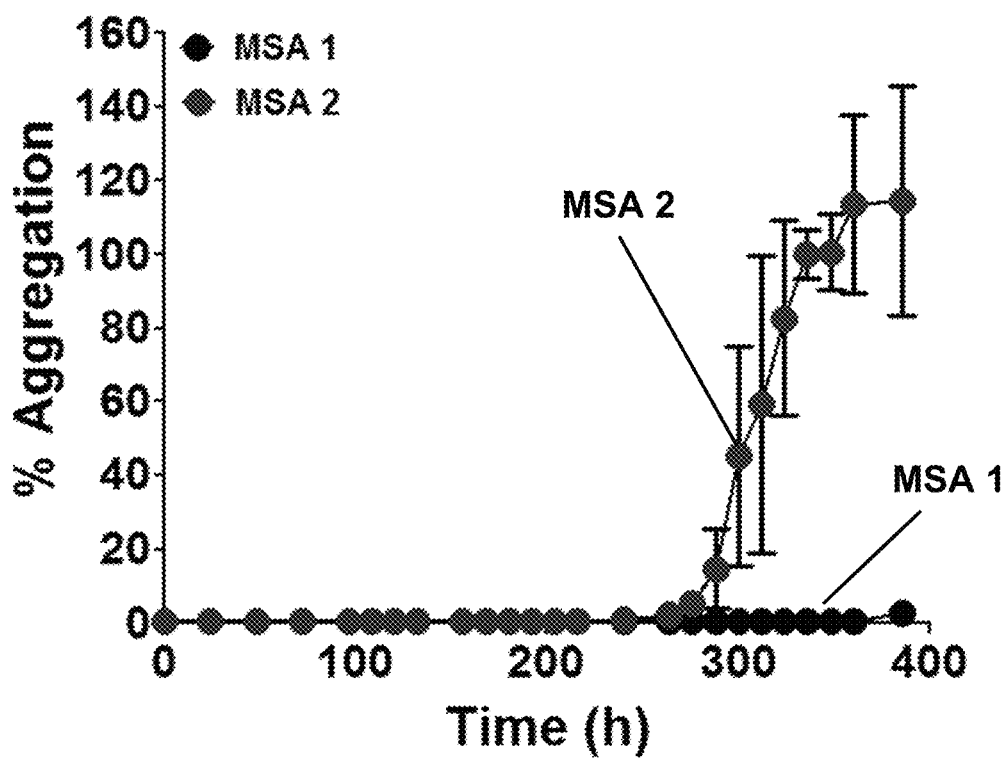
FIG. 6C is a graph that shows the results in patients with Multiple System Atrophy (MSA) for the detection of αS seeds in CSF samples.

Example 6

αS-PMCA Detects Oligomeric αS in the Cerebrospinal Fluid of Patients Affected by Pd and Multiple System Atrophy with High Sensitivity and Specificity To study the efficiency of αS-PMCA for biochemical diagnosis of PD and related α-synucleinopathies, such as multiple system atrophy (MSA), tests were performed on CSF from many patients affected by these diseases as well as controls affected by other diseases. FIGS. 6A, 6B, and 6C show detection of seeding activity in human CSF samples from controls and patients affected by PD and MSA, respectively, using αS-PMCA. Purified seed free alpha-synuclein (100 μg/mL) in buffer MES, pH 6.0 was allowed to aggregate at 37° C. with shaking at 500 rpm in the presence of CSF from human patients and controls. The extent of aggregation was monitored by Thioflavin T fluorescence at 485 nm after excitation at 435 nm using a plate spectrofluorometer.

Test CSF samples were obtained from patients with the diagnosis of probable PD and MSA as defined by the DSM-IV and determined using a variety of tests, including routine medical examination, neurological evaluation, neuropsychological assessment, and magnetic resonance imaging. CSF samples were collected in polypropylene tubes following lumbar puncture at the L4/L5 or L3/L4 interspace with atraumatic needles after one night fasting. The samples were centrifuged at 3,000 g for 3 min at 4° C., aliquoted and stored at −80° C. until analysis. CSF cell counts, glucose and protein concentration were determined. Albumin was measured by rate nephelometry. The study was conducted according to the provisions of the Helsinki Declaration and was approved by the Ethics Committee.

The experiments as well as the initial part of the analysis were conducted blind. FIGS. 6A, 6B, and 6C are graphs of αS aggregation versus time, measured as a function of ThT fluorescence labeling, showing the average kinetics of αS aggregation, respectively, for controls and two representative samples from the PD and MSA groups.

The results indicate that CSF from PD patients significantly accelerates αS aggregation as compared to control CSF ($P<0.001$). The significance of the differences in αS aggregation kinetics in the presence of human CSF samples was analyzed by one-way ANOVA, followed by the Tukey's multiple comparison post-test. The level of significance was set at $P<0.05$. The differences between PD and samples from the other two groups were highly significant with $P<0.001$ (***).

The outcome of the overall set of 29 PD or MSA samples and 41 controls was that 26 of the 29 PD or MSA samples were positive, whereas 3 of the 41 control samples were positive, which corresponded to a 90% sensitivity and 93% specificity.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto." To the extent that the term "selectively" is used in the specification or the claims, it is intended to refer to a condition of a component wherein a user of the apparatus may activate or deactivate the feature or function of the component as is necessary or desired in use of the apparatus. To the extent that the term "operatively connected" is used in the specification or the claims, it is intended to mean that the identified components are connected in a way to perform a designated function. To the extent that the term "substantially" is used in the specification or the claims, it is intended to mean that the identified components have the relation or qualities indicated with degree of error as would be acceptable in the subject industry.

As used in the specification and the claims, the singular forms "a," "an," and "the" include the plural unless the singular is expressly specified. For example, reference to "a compound" may include a mixture of two or more compounds, as well as a single compound.

As used herein, the term "about" in conjunction with a number is intended to include ±10% of the number. In other words, "about 10" may mean from 9 to 11.

As used herein, the terms "optional" and "optionally" mean that the subsequently described circumstance may or may not occur, so that the description includes instances where the circumstance occurs and instances where it does not.

In addition, where features or aspects of the disclosure are described in terms of Markush groups, those skilled in the art will recognize that the disclosure is also thereby described in terms of any individual member or subgroup of members of the Markush group. As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, and the like. As a non-limiting example, each range discussed herein can be readily broken down into a lower third, middle third and upper third, and the like. As will also be understood by one skilled in the art all language such as "up to," "at least," "greater than," "less than," include the number recited and refer to ranges which can be subsequently broken down into sub-ranges as discussed above. Finally, as will be understood by one skilled in the art, a range includes each individual member. For example, a group having 1-3 cells refers to groups having 1, 2, or 3 cells. Similarly, a group having 1-5 cells refers to groups having 1, 2, 3, 4, or 5 cells, and so forth. While various aspects and embodiments have been disclosed herein, other aspects and embodiments will be apparent to those skilled in the art.

As stated above, while the present application has been illustrated by the description of embodiments thereof, and while the embodiments have been described in considerable detail, it is not the intention of the applicants to restrict or in any way limit the scope of the appended claims to such detail. Additional advantages and modifications will readily appear to those skilled in the art, having the benefit of the present application. Therefore, the application, in its broader aspects, is not limited to the specific details, illustrative examples shown, or any apparatus referred to. Departures may be made from such details, examples, and apparatuses without departing from the spirit or scope of the general inventive concept.

The various aspects and embodiments disclosed herein are for purposes of illustration and are not intended to be limiting, with the true scope and spirit being indicated by the following claims.

The invention claimed is:

1. A method for determining a presence of a soluble, misfolded alpha synuclein (αS) protein in a human cerebrospinal fluid (CSF) sample, the method comprising:
   (1) contacting the CSF sample with a pre-incubation mixture, the pre-incubation mixture comprising:
      (i) seed-free monomeric αS substrate in a concentration range of from about 1 μM to about 10 μM;
      (ii) a buffer composition having a pH between about 6 and about 8.5;
      (iii) NaCl in a total concentration of about 500 mM; and
      (iv) thioflavin T (ThT),
   to form an incubation mixture;
   (2) conducting an incubation cycle two or more times on the incubation mixture effective to form an amplified portion of misfolded αS protein from the seed-free monomeric αS substrate, each incubation cycle comprising:
      (i) incubating the incubation mixture effective to cause misfolding and/or aggregation of at least a portion of the seed-free monomeric αS substrate in the presence of the soluble, misfolded αS protein, the incubating being conducted at a temperature of about 37° C.;
      (ii) shaking the incubation mixture for about one minute at about 500 rpm effective to at least partly de-aggregate at least a portion of a misfolded αS aggregate, followed by about 29 minutes without shaking, and
   (3) determining the presence of the soluble, misfolded αS protein in the sample by detecting at least a portion of the amplified portion of misfolded αS protein, the detecting comprising measuring ThT fluorescence at about 485 nm after excitation at about 435 nm, wherein:
(i) the soluble, misfolded αS protein comprises one or more of: a soluble, misfolded αS monomer and a soluble, misfolded αS aggregate; and
(ii) the amplified portion of misfolded αS protein comprises one or more of: an amplified portion of the soluble, misfolded αS monomer, an amplified portion of the soluble, misfolded αS aggregate, and an insoluble, misfolded αS aggregate.

2. The method of claim 1, the subject being treated with one or more of:
an αS modulating therapy, further comprising:
comparing the amount of the soluble, misfolded αS protein in the CSF sample to an amount of the soluble, misfolded αS protein in a comparison sample, the CSF sample and the comparison sample being taken from the subject at different times over a period of time under the αS modulating therapy; and
determining that the subject is one of: responsive to the αS modulating therapy according to a change in the soluble, misfolded αS protein over the period of time, and non-responsive to the αS modulating therapy according to homeostasis of the soluble, misfolded αS protein over the period of time; and
a disease-modifying therapy for Parkinson's disease (PD), further comprising:
comparing the amount of the soluble, misfolded αS protein in the CSF sample to an amount of the soluble, misfolded αS protein in a comparison sample, the CSF sample and the comparison sample being taken from the subject at different times over a period of time under the disease-modifying therapy for PD; and
determining that the subject is one of: responsive to the disease-modifying therapy for PD according to a change in the soluble, misfolded αS protein over the period of time, and non-responsive to the disease-modifying therapy for PD according to homeostasis of the soluble, misfolded αS protein over the period of time.

3. The method of claim 2, further comprising treating one or more of the subject determined to be responsive to the αS modulating therapy with the αS modulating therapy and the subject determined to be responsive to the disease-modifying therapy for PD with the disease-modifying therapy for PD.

4. The method of claim 1, further comprising treating the subject with an αS modulating therapy to inhibit the production of αS or to inhibit the aggregation of αS.

5. The method of claim 1, the shaking comprising cyclic agitation.

6. The method of claim 1, the seed-free monomeric αS substrate and/or the soluble, misfolded αS protein comprising one or more of: one or more peptides formed via proteolytic cleavage of one or more of αS-140 protein; αS-140; αS-126; and αS-112.

7. The method of claim 1, wherein the concentration of the seed-free monomeric αS substrate is about 7 μM.

8. The method of claim 1, wherein the buffer composition has a pH of about 7.4.

9. The method of claim 8, wherein the buffer composition comprises PBS.

10. The method of claim 8, wherein the buffer composition comprises HEPES.

11. The method of claim 8, wherein the buffer composition comprises Tris HCl.

12. The method of claim 1, wherein the buffer composition has a pH of about 6.

13. The method of claim 12, wherein the buffer composition comprises MES.

14. The method of claim 12, wherein the buffer composition comprises PIPES.

15. A method for determining a presence of a soluble, misfolded alpha synuclein (αS) protein in a human cerebrospinal fluid (CSF) sample, the method comprising:
(1) contacting the CSF sample with a pre-incubation mixture, the pre-incubation mixture comprising:
(i) seed-free monomeric αS substrate in a concentration range of from about 1 μM to about 10 μM;
(ii) a buffer composition having a pH of about 7.4;
(iii) NaCl in a total concentration of about 500 mM; and
(iv) thioflavin T (ThT),
to form an incubation mixture;
(2) conducting an incubation cycle two or more times on the incubation mixture effective to form an amplified portion of misfolded αS protein from the seed-free monomeric αS substrate, each incubation cycle comprising:
(i) incubating the incubation mixture effective to cause misfolding and/or aggregation of at least a portion of the seed-free monomeric αS substrate in the presence of the soluble, misfolded αS protein, the incubating being conducted at a temperature of about 37° C.; and
(ii) shaking the incubation mixture for about one minute at about 500 rpm effective to at least partly de-aggregate at least a portion of a misfolded αS aggregate, followed by about 29 minutes without shaking; and
(3) determining the presence of the soluble, misfolded αS protein in the sample by detecting at least a portion of the amplified portion of misfolded αS protein, the detecting comprising measuring ThT fluorescence at about 485 nm after excitation at about 435 nm, wherein:
(i) the soluble, misfolded αS protein comprises one or more of: a soluble, misfolded αS monomer and a soluble, misfolded αS aggregate; and
(ii) the amplified portion of misfolded αS protein comprises one or more of: an amplified portion of the soluble, misfolded αS monomer, an amplified portion of the soluble, misfolded αS aggregate, and an insoluble, misfolded αS aggregate.

16. The method of claim 15, wherein the concentration of the seed-free monomeric αS substrate is about 7 μM.

17. The method of claim 15, wherein the buffer composition comprises PBS.

18. The method of claim 15, wherein the buffer composition comprises HEPES.

19. The method of claim 15, wherein the buffer composition comprises Tris HCl.

20. A method for determining a presence of a soluble, misfolded alpha synuclein (αS) protein in a human cerebrospinal fluid (CSF) sample, the method comprising:
(1) contacting the CSF sample with a pre-incubation mixture, the pre-incubation mixture comprising:
(i) seed-free monomeric αS substrate;
(ii) a buffer composition having a pH of about 6.0;
(iii) NaCl in a total concentration of about 500 mM; and
(iv) thioflavin T (ThT),
to form an incubation mixture;

(2) conducting an incubation cycle two or more times on the incubation mixture effective to form an amplified portion of misfolded αS protein from the seed-free monomeric αS substrate, each incubation cycle comprising:
   (i) incubating the incubation mixture effective to cause misfolding and/or aggregation of at least a portion of the seed-free monomeric αS substrate in the presence of the soluble, misfolded αS protein, the incubating being conducted at a temperature of about 37° C.; and
   (ii) shaking the incubation mixture for about one minute at about 500 rpm effective to at least partly de-aggregate at least a portion of a misfolded αS aggregate, followed by about 29 minutes without shaking; and
(3) determining the presence of the soluble, misfolded αS protein in the sample by detecting at least a portion of the amplified portion of misfolded αS protein, the detecting comprising measuring ThT fluorescence at about 485 nm after excitation at about 435 nm, wherein:
   (i) the soluble, misfolded αS protein comprises one or more of: a soluble, misfolded αS monomer and a soluble, misfolded αS aggregate; and
   (ii) the amplified portion of misfolded αS protein comprises one or more of: an amplified portion of the soluble, misfolded αS monomer, an amplified portion of the soluble, misfolded αS aggregate, and an insoluble, misfolded αS aggregate.

21. The method of claim 20, wherein the buffer composition comprises MES.

22. The method of claim 20, wherein the buffer composition comprises PIPES.

* * * * *